(12) United States Patent
Cerrato et al.

(10) Patent No.: US 12,110,556 B2
(45) Date of Patent: Oct. 8, 2024

(54) KIT FOR ASSESSING THE RISK OF COMPLICATIONS IN PATIENTS WITH SYSTEMIC INFLAMMATORY RESPONSE SYNDROME (SIRS)

(71) Applicants: BIOMERIEUX, Marcy-l'etoile (FR); HOSPICES CIVILS DE LYON, Lyons (FR); UNIVERSITE CLAUDE BERNARD LYON 1, Villeurbanne (FR)

(72) Inventors: Elisabeth Cerrato, Lyons (FR); Benjamin Delwarde, Lyons (FR); Guillaume Monneret, Lyons (FR); Estelle Peronnet, Lyons (FR); Julien Textoris, Villeurbanne (FR); Fabienne Venet, Lyons (FR)

(73) Assignees: BIOMERIEUX, Marcy-l'Etoile (FR); HOSPICES CIVILS DE LYON, Lyons (FR); UNIVERSITE CLAUDE BERNARD, Lyons (FR)

( * ) Notice: Subject to any disclaimer, the term of this patent is extended or adjusted under 35 U.S.C. 154(b) by 0 days.

(21) Appl. No.: 17/729,115

(22) Filed: Apr. 26, 2022

(65) Prior Publication Data
US 2022/0259661 A1     Aug. 18, 2022

Related U.S. Application Data

(62) Division of application No. 15/780,573, filed as application No. PCT/FR2016/053164 on Dec. 1, 2016, now Pat. No. 11,339,438.

(30) Foreign Application Priority Data

Dec. 1, 2015    (FR) ...................................... 15 61671

(51) Int. Cl.
*C12Q 1/6883* (2018.01)
*C12Q 1/6806* (2018.01)
*C12Q 1/686* (2018.01)

(52) U.S. Cl.
CPC ......... *C12Q 1/6883* (2013.01); *C12Q 1/6806* (2013.01); *C12Q 1/686* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2013/0190194 A1* 7/2013 Tang .................. G16B 20/00
                                                                    435/6.12

* cited by examiner

*Primary Examiner* — Katherine D Salmon
(74) *Attorney, Agent, or Firm* — LADAS & PARRY LLP; Malcolm J. MacDonald, Esq.

(57) ABSTRACT

A kit for in vitro measurement of a at least one IL7R gene transcript in a blood sample, including specific reagents for measuring the transcript, and a control sample calibrated to contain the IL7R gene transcript corresponding to the mean quantity measured in a pool of reference blood samples from human patients in a state of septic shock when reference blood samples are taken, or who were in a state of septic shock within 72 h after taking the reference blood samples, and who were known to have survived, and/or a calibrated to contain the quantity of an IL7R gene transcript corresponding to the mean quantity measured in reference blood samples from patients in a state of septic shock when the reference blood samples are taken, or who were in a state of septic shock within 72 h after taking the reference blood samples, and not to have survived.

Figure 1:
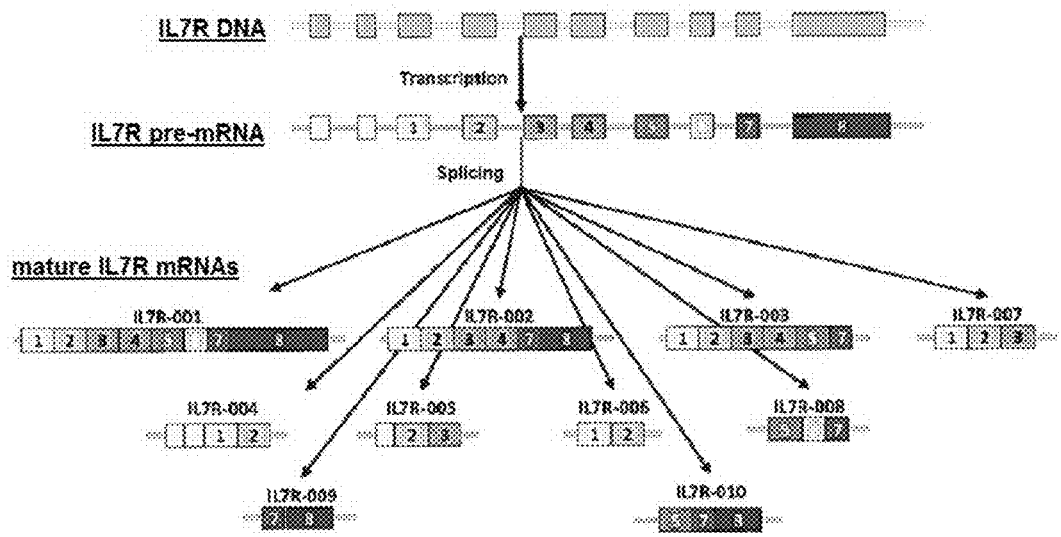

6 Claims, 3 Drawing Sheets
Specification includes a Sequence Listing.

SEQUENCE LISTING

<160> NUMBER OF SEQ ID NOS: 20

<210> SEQ ID NO 1
<211> LENGTH: 22729
<212> TYPE: DNA
<213> ORGANISM: Artificial Sequence
<220> FEATURE:
<223> OTHER INFORMATION: IL7R gene

<400> SEQUENCE: 1

| | | | | | |
|---|---|---|---|---|---|
| atctaagctt | ctctgtcttc | ctccctccct | cccttcctct | tactctcatt | catttcatac | 60 |
| acactggctc | acacatctac | tctctctctc | tatctctctc | agaatgacaa | ttctaggtac | 120 |
| aacttttggc | atggtttttt | ctttacttca | agtcgtttct | ggagaaagtg | gctatgctca | 180 |
| aaatggtgag | tcatttctaa | gttttcttat | ggattttgga | ttatctgtag | catggtttca | 240 |
| ggttattcag | ttccctaaca | gacctgagtc | aggcactggg | tttgaatgca | gtttgagaat | 300 |
| ttcccacata | ttcagtcatt | ttttttaatg | tttaaccacc | atgacagggg | gcaggggatc | 360 |
| aatactatgg | gtggtttata | agacctcagt | attctcaaga | aggaatgcat | ttcactccca | 420 |
| agtgtagatc | ttaaatgttg | aatgattact | ctgctcttac | aaaaagaatg | ctcatgtaga | 480 |
| tgctatgact | gtacttgtag | gaaaatgtcc | aaagtaattt | taccttgtca | ggagatcaaa | 540 |
| ctggattcat | tttgtttgac | tttttaagaa | atcctgaaag | cataactttc | aggataaggt | 600 |
| aatgtacaga | agcaatagct | ttgtcttcag | tgaccagtgc | tatatcctca | gcacctaaat | 660 |
| cagtggctag | aatatagtag | acatccaata | acttttgaaa | gtgttttcaa | aatactttag | 720 |
| ttttgagaga | tttatgtgag | attttaagta | aataactgac | tagagaaaga | tctaaatgag | 780 |
| tttactcatt | gaaatacact | gaattgcctc | cacaccaaca | aattggccat | atgtaataat | 840 |
| tctttttggg | atctaaaaaa | cttagtaccg | agaagccaac | cctgcccata | cataaacaca | 900 |
| ttgtaattat | aacaaaacta | ggcagaagct | tctaacagca | gcaggaggca | tgtgggaatt | 960 |
| tagaccatca | acttgctcct | gcaaattaag | ccctttctct | ttaagagtta | aaaactattt | 1020 |
| ggctatagac | aatatcaaac | acatcagcct | aatgactcag | cttatgcatt | ttgagtcatg | 1080 |
| taattacgaa | ggatggaaat | ccctagaatt | ttctcattaa | gggaattgtc | agagagtttg | 1140 |
| acattttta | cagtatatga | ctcactttat | ggggatgat | tattattcta | tgctaaactt | 1200 |
| tgccttggat | ttccacaaag | actgatggga | ggcaggaaac | ataaatctta | ctctctttca | 1260 |
| tgtcatctat | actcactagt | tcaccctggt | gatcatacta | ttttttaaat | atataagaat | 1320 |
| gctagttgaa | agctgggttt | tcactccaac | tttttaagtt | tcagattttt | tagaagatgt | 1380 |
| ataattaccc | tattcacatg | attacgtcaa | aatacttccc | agtttggggt | ataggaattc | 1440 |
| acattcagtt | gctgcttgtt | gaaagttgtc | aattttctga | tcatcacaag | gatgatcaag | 1500 |
| agaagaaagg | gatactttt | aaaaatccaa | atcatttaca | ctattaatca | actaactcca | 1560 |
| ttcagtagga | agaagacttc | tagatgacac | tggcttgcct | atgatacata | ttccacacaa | 1620 |
| tttaaatttt | tatggataaa | tatgtctaga | tacctatttaa | aatatgaata | atattaatta | 1680 |
| ttgagcattt | aaagaataat | agattaactc | attattcaaa | agctctatgt | aatttcaaaa | 1740 |
| ccatagtaat | tataacaccg | tcaattgaca | taaacttttt | aaagagaagc | tcaaatgttt | 1800 |
| catgtatatt | ttcagaatta | gaattcttat | tttacctttt | cattacttat | ttctcagaaa | 1860 |
| atattatact | catagctaat | ccctattaaa | tccttactgt | gttctaagct | acctctttgt | 1920 |
| aaatatccat | tcagtgattg | ctcatagcac | gagtttacat | attagaacac | atgtcttaga | 1980 |
| gaagttgcct | acctgacaga | ggaccacagg | tagagtatcc | agaatttaaa | cgcacatctg | 2040 |

```
tccagctcta acaccacagg tcttaaccac tgtgtacatt aactactctt agccaagaat    2100
ttttcagctc acgtcatgta gaatattctt tttgtaaaat gccatcacat tttataagtc    2160
attgaaggga attttcttg gttacaaagc aactctgccc cataatatct actgaaaagc     2220
cagtgagctg cttcctaaaa cacagccatt ttaggtgcag gaaacagtgt ataaatggct    2280
cattgtatat tgtatgcttt gccagactga gtggcagtgg gagtcctttg ttatgtgggt    2340
gctgacatct gctagagtgt gctgtctcta ttgaagaatc gtgaagacaa agccgaccca    2400
caggatgtct gaatccaaat aataatacat gttctgtgta tagaattggt ggaagagaaa    2460
atgtcaggac agtgtgagga ctgccatgta aggtcagaac cactgcattt agaaagctac    2520
cactgcacag ggaagaaatc taagtctaca aaattagtgg gctgtctctc attatttcgt    2580
gctgtcatca aaggagggc catacccctgc tgaaactaca taaagagctt ttgctggtgg    2640
cagaactgtg aactggatgg attctgggaa tggccagaaa acaaatgcc tgtggttgtg     2700 agcagtgccc acacccatgg tctagctagg gctgtttgag atttgttgct ttgactgaac    2760
caacctgtca ttcaactggt tggtccattc acagtcagct ttattaactt tcccatttc     2820 cctactgagt tatttaagta aagaaagtgc tattcggaca gcccttggtc tctgggacaa    2880
tcaactggga tttgattta gtatattctg tctccagtgt aaagccttgg aagcatctaa    2940
tttctagtac tgatgaacca aaaatacatg gaagcagtcc taggctcaca cttgagcact    3000
ctgagaatgg ctttgcttac tccagatttt ctcaggtccc agtgggtgta tattttctga    3060
catatttatt ccagcctcac tttctatcat gtaaaacata catacaaaat gtagatttca    3120
ttatagggtc tacaaaacag cttaagaaac caaatactat gtgtgacaga tcacactttc    3180
caaaagtaat agcaaaaaaa aaaaaaatct ggttccccac tttcttccag catcctgcta    3240
gaatctatca gatactgcgt ctatagaaga atctataaga acagaagcag tatgtacaac    3300
attcacagga agtttcacca aatcggagtc ctgccagatc taattttttt tccctaatca    3360
cgtttgtctc agtcagtagc ttaagacaat ggaaataatc agtgccactt ttaattggga    3420
tgccttttta ggcaagggaa agtgacctct aaaaaagca aaattctgac tgcaagatag     3480
ctatcattgt ccttcattta agacaaaaaa aatactaggg agggaataaa ttatgatttg    3540
taataaagtg aaaagtgaga ttaggtagca tggggataat ggaaataaag tgtctcttct    3600
ttgaaataat atgaacaatc aatgtaacaa atgtagcaga aaaaactcca gtttaaatac    3660
agaaaagaat gtgttcaatg cctctggttc tttaactcag aaatatttgg aggttactta    3720
ctcattatga tggattttt ttttctattg gaaaactctg ttagcattga gcgttttgt      3780 tttttgtttt ttgttggttg gttggttttg aagcattttt cttgtctttg cccttgggct    3840
tttcttcctt gaatactaca taatccatta ctatttcatg tctgccacag agtctgctat    3900
tttattaagg tcatgccata tttcaaaagg atgcatttat ttgtttcatt aacagctgca    3960
tgtttgttcc tccccaggag acttggaaga tgcagaactg gatgactact cattctcatg    4020
ctatagccag ttggaagtga atggatcgca gcactcactg acctgtgctt ttgaggaccc    4080
agatgtcaac atcaccaatc tggaatttga aatatggtga gggatggtgg ttttaatggt    4140
tgcttagaca tcctctgtct ctcttttcat atgctctttt taatagccac aaaagaaaga    4200
atatgtggcc taattaacaa atgttaacat ctaaggaatt cccaaaggcc tcctgaaact    4260
ccttgtcctt caccaaaaac actcatacaa atctcctctc acggttcagc tttcagaccc    4320
tgagactcag tcaaatgatg ctctggatct tggggatccc acatccctcc caacttcata    4380
```

```
tcagaattta atcctgcgt ctcctacaac acttctcacc aaaaatctgt ttgcccaaca    4440
cgagacaatc cagtgtcttc aagttgcatc tgagagttaa actgccttgt ttccaatccc    4500
aataccagtg cttactagtt ttttgaccta gagaaagtta tgtaatgtat ctatgcctca    4560
gtttcctcac ctgtaaaatg agataacctg cctcacagga aggctgtgat ggttaaataa    4620
tttcatcata taaatcattc caaatagtcg gccagtgaat aacgagtaat ggggaagcaa    4680
cattaaatta taattctgtg aatattgacc taacttctac catcttgaca caatttgact    4740
tcagatgatc ctctcaatgt aaattttcca aaaatccaca ggaataagtt ggcattttgt    4800
ttcacaaggt ctcacagaaa agacaaagga aaagagtctg gtttgaaagt ttactaaagg    4860
tctcagggaa ctttatcttc tccttctcct tcatccataa gtcatctctt gttgccaagg    4920
gttactatct ctggtgattt gagaaactac tctagcttga aattctgacc tgaggctatc    4980
tccaaattca tatccgaatg acctactttt tagttagtgt cctagtgagc aaagtaaatc    5040
aagatccacc agtagtaata gaaggcttcc tacattccat agacactgag acaattctcc    5100
acagtctata gtccaaacaa gccctgaatt ccagtttttg tcaatttatg ggagcttcct    5160
gcatctattt atggagtgct ttctgctgca gtccttagat aaacatgctg ttggacttga    5220
gtagtgtact gtgttctctg tctgcctctg ttcacttccc taacacattt tccaggaata    5280
aaatatgtca aaagaacctg aaccagttcg atgtccacaa tctaggctgg aaatggattg    5340
cactaaaaca gccataacaa ctcattcaaa caaggcactc attttcatgg gcaaatcact    5400
ctcccacacg gaggtttgac tttggcttct ttaaccagct ggctggtggg ctgagtgttc    5460
atcctggttt ctcttggcca agctgaggtt gacctttctg ttcactttca ttcacaccat    5520
atttgaccac ttccttgccc actcaaacat acttacccctt taacatatct cttgactttt    5580
cctgtcatat tgtaatctgt ccagagcctc ctctatttgg gttttccaat tggattcaga    5640
tatttcagtt ggaaagggac tgccttaaga aagaaacgtt ttcagtggaa aatatatgta    5700
tgagctcttt aatagatgaa ctcctggagt tcagagccct taaaaggatg cccagtttca    5760
caagacagcc atacggtcat ccttgattgt ccattgctca ttaatttcat tctcaaaatc    5820
atgggaatga gctgagaata ccattttaga tcctccttaa attcccaaca gtaccagaaa    5880
cttgctacag gttggggcct gtaattggat atttcacaca tactttcctt acaaatatat    5940
tctatactca agaattgaac taaaagttat tgtcctagtt tctccacatc ccatgtttac    6000
ctaaaattca gaaatgggac cccgctccca gtctcccctt ctatatttat ttatcaaatc    6060
gtgacaacat taccatcttc agatctttcc acctgatgtt tgtcctaagc ttattccctg    6120
gtatctgtct agcttaccca aaaattcggt ttttattttt atcctgttcc aagttgggaa    6180
agcctatcta ccccaacaag gaacacaact ccctagtaac tttgagacac acacacacat    6240
acacacctac tctttaaagc ctaaacaatc gcacactcta aagatagca gttaacaaaa    6300
gtaacgattt gggagaacag ttttaaggaa tgtccccaaa ataatcaata catttagcca    6360
gttaattaac ttaacatttc ttcaccaatc tctagttttc atgactgtag gagcttaacc    6420
agtcactctc agaccacaat aaaccaaagg tgaaagattc tgtaacaaaa gctagggcac    6480
tctcccctgc atttaacctc ctggccagct cactcgaagc cagacaaaca ggttcctctt    6540
tttgtgcaga gtccaggaac cattctcgaa aggactcatt tgagcacatg cagagaagag    6600
tgtacacaca tccagttcac caagggaagc caacacacat tgtgggttgt aggtagtaaa    6660
aggccttcct agaacacact ccttaggatt taaacaaaat tacatcggtt aatggaaaga    6720
attcttttcat atacgcaaac ttacccagag gaacttttct tctgcccaga tcttcacttc    6780
```

```
caatttgacc cagttatacc tctttagagc tatttggctg agcttaaaca gcacatagga    6840
aaaacaaatt ggtaactgtg tttatcacag aagaggaaaa ttaaatttag ggttgggaaa    6900
ggaaaataac cctatgatat tactttttatt ctacctttac aatgagaata tatacctttg   6960
ttacttcttt aatttttaca ttatttactt attttttcttt gctttcttgt ttgattacaa   7020
tgcattttag gggtaaaatt tatgtgtggt aaaatgcaca aaaattaagt gaatttggag    7080
aaatgtctat gacctgtagc cattccaatg gtaaagatat agaacttatt tttcccctag    7140
aaggatgctt catgttcctt tccagtcaat cttcataccc caggagcaat cataattctc    7200
aattctatta ccctttggtt tttgccagtt tctgatagtt cttattaata gaatactctt    7260
tattcttttc tgtcttcttt catttaacca gtgtttgtga gagttagcca tgttgatgtc    7320
catctcatag ctcatctttt caattgctaa gtagtaattc cactgtatga atataccaca    7380
aatttttaat tctttctctt cttgatgaac atttgtgttt tttcaagttt gagactatta    7440
ttttttaggt tgctgttcac attcttggac aaatcagttt gtgtatatat attttcattt    7500
ttctggggta taaaacctca gaatggaatt gctgtgtcat aaggtaagca tgtatctaag    7560
tttataagaa accgcccaac agttttcaa agtggttata ccattctact ctccttccag     7620
cgatgcatga gagatataca tcatttgcaa cgtttgactt gggatagta tctcgttagg     7680 ttttttaattc gcatttgtca ataacaaat gttgagcagc ttttcatata cttggtcttt    7740
tgcctgtctt ctttgggcta gtatctgtta aaagcactga gttatttgtc cttttgttat    7800
tgctggatat gagttctttta tacattctgt atacatttcc tttgtcagat agatgtattg   7860
catctatttt ctattctgaa gtttgccatt ttattttctt actggtgcgt tttaataagc    7920
aagagttttt ttttattttg atggagtcta atatatcatt tattttcttt tatatgtagt    7980 gcttttttgta tccttgctaa gataactttg cctactccca aagttgggaa gatattttct   8040
catgttttct tttaaatgtt ctacagtttt agcctttata tttagttttt ttaattatta    8100
ttatacttta agttctaggg tacatgtgca caacgtgtag gtttgttaca tatgtataca    8160
tgtgccatgt tggtgtgctg caccgattaa ctcgtcattt acattaggta tatctcctaa    8220
tgctatccct cccccctcct tccacctatg actggccctg gtgtgtgatg ttcccccttcc   8280 tgtgtccaag tgctcttatc gttcaattcc catctatgag tgagaacatg cagtgtttga    8340 tttttttgtcc ttgtgatagt ttgctgagaa tgatggtttc cagcttcatc catgtcccta   8400
taaaggacat gaactcatcc tttttatgg ctgcatagta ttccatggtg tatatgtgcc     8460 acattttcttt aatccagtct atcattgatg gacatttggc ttggttccaa gtctttgcta   8520
ttgtgaatag tgctgcaata atcgtacatg tgcatgtgtc tttatagcag catgatttat    8580
actcctttgg gtatataccc agtaatggga tggctgggtc aaatagtatt tctagctctg    8640
gatccttgag gactcgccac actgtcttcc acaatggttg aactagttta cagtcccacc    8700
aacagtgtaa aagtgttcct atttctccac atttccctcca gcacctttttg tttcctgact  8760 tttaatgat caccattcta actggtgtga gatggtatgt cattgtggtt tgatttgca     8820 tttctctgat ggccattgat ggctaatatc cagaatctac aatgaactca aacaaattta    8880
caagaaaaaa acaaacaacc ccatcaaaaa gtgggcaaag gatatgaaca gacacttctc    8940
aaaagaagac atttatgcag ccaaaagaca catgaaaaaa tgctcatcat caatggccat    9000
cagagaaacg caaatcaaat tgtgtttatt tgtttctctt gtcttatgca ttggctaaaa    9060
cctcctgtac accactgaat agaaatggtg aaagtggata ttcctgtcgt gtcctggtct    9120
```

```
tagggaaaca attcatgttc acaatttcag cactaaatat gatattaact ataggctttt    9180
gtaaatgctc tttatcagat tgaggaagtg tctttctatt tcttatttgc tgtgagtttt    9240
taacatgaat agatgcattc atgttattaa attatgcttt gaatgcattg attgattata    9300
accaggttat ttatgtcttc tagtctgtta acatggcaaa ttatattgat taattttga    9360
atctttaacc tgctttggtt tcctgagatg tgccctactt tataattatg tattaaaatt    9420
agtgtgttag tattttcttg tgaaagtttg cttatacatt tttgagggat atttgtctat    9480
caacttcttt tctctaatat tttggccagg tttgggtacc aggattaagc tagcttcaaa    9540
aaataggttg agaagggtca ttcctcttcc agtttctaaa ataatttgtg tcagattgac    9600
actatttctt tccttataca tttgatagaa tttaccagaa tataaccatc aagcatagag    9660
ttttctttgg ggggaagttt attgataata agtttaattt ctttgagaga aatataactg    9720
ttgaaatatt ccatttctat gtgggtcaga tttactaatt tgtgtttata aaaacattt     9780
cattacatct aagttattat atacattaaa atagcattta aaatttcctt attatacttt    9840
taacatctgc atgttctata gtgatatctc ctcttacatt ccagatatta gtaatttata    9900
tattttgttt tcttaaccac tcttgttagg gttcaccagc caaaattacc tataaaaatc    9960
cattacgtta cccatcaagt atatgtgata ttatgtatat aacccttat actatgttat     10020
catttcttt aacactttt ttaatcaata ttttttacag ctcttatttc ttacatatat     10080
tcctatggaa catcaaaaaa agcaattact ttttaatcta aacaaagtat ttgttttca    10140
gtgatcaatt ataaaaatat agaaatttcc cataatttta taaatatgtc ttgactattt    10200
caggttcaat tgcatctaat tctaagtaaa tcatcactaa gtatcatagc agcagaaagc    10260
cataagattt taattcatta tctctcattc ctgaacatgc ctccactcac ccacccacat    10320
acctatgaac agagttaaag tcaaacatac atcaatgtgc atatgatact attccactgc    10380
atacaggaac tcctacctga atcaagacat atccccttt tattcctaca gtggggccct     10440
cgtggaggta aagtgcctga atttcaggaa actacaagag atatatttca tcgagacaaa    10500
gaaattctta ctgattggaa agagcaatat atgtgtgaag gttggagaaa agagtctaac    10560
ctgcaaaaaa atagacctaa ccactatagg taagaagttg tatataaaag tatggttgtc    10620
acttttgggc tacctgaaaa cactgtgtct ggacattctg taggttaaaa gtagacaaat    10680
agtggaaaca actggcaata gataatagct aattccctac tgtaaatttt tataataaat    10740
gaaaagcttg aaatttatac tttcctgcag tgaaagaatt ctgaggatct tcaaacccag    10800
gtgtgaaaga tagtgtttgt gcaaacctac atgaagtggc taactggagc tgggcttcct    10860
gtcatccatc acaggtgtcc tttccttcct tatctgtcct ttccttcctt acctgtcctt    10920
ctcccaaatt ccttgtggtc ttctcccaa atccccacaa cattctgagt aagtttagct    10980
aacttatcaa gttatttta aaagcatata tgccttctct attagtcaga gttttctaca    11040
aaaaaaaaag ggaatcaata ggaggataga tagatagatc attgatagga gagatttcta    11100
ttaagaaatt gacttttgtg gttgtgggaa ctggcaatcg caaaaatcca taaggcaagc    11160
cagtaggcta gaaattcagg aaagagtgca gtattgagcc taaattccgc agggcaagaa    11220
actcaagcag attttctgta ttgtactctt gagacagact tgcttcttct tcagggaacc    11280
tctgtctttg ctctagaggc cttctactga tgaggtgatg cccaccacat cacggaaggc    11340
aatctacttt actcaaagtt tactgattta aatgttaacc atgtcttaaa aatactttta    11400
gcattcccta ttcgctcccc cttcaaccct caaaaagaaa attaaggta agagagcaat     11460
actcattaga gataagaaag agtaagaaac ctagctcagc tttgtctcag ttttgtttca    11520
```

```
ctaagatgat aaaatagaga ggtaaagcag aagttccatg tgtgaacaat taacttgtga   11580
aaaggcaaat gtagtagaaa agagacatta ggcagatggc tgtgcatgtt ggccacacag   11640
aagcagcatt ggccatgacc agtgtgggtc ctggttaggg aagagaact  ggctttgaca   11700 acaacagggt atctctgagg ttataaaaag ttgggttctg atcatttgga gatgaggtcc   11760
ctatggatag ggcaccatat ctaaaggttc accatttaca ttgcaaatat acattcagtt   11820
ctctgagagt gagcagagaa ggcagaggtt ctcagtcttc tgacaaggtc ctggagcatc   11880
aggggagagc ccattcttac aaaactccac accagcatgc aagcccttac atgcacataa   11940
gcactcacaa cacaccaaga gcctccaggt gacatctgcc acctccaaat ccccatatcc   12000
cacatgctca atgcacttgc agtctccatc ccccagcaga ctgcaaatct gacatgcctc   12060
ctccgaacgg caaggggag  aggtacgtat ggtacacaca ctgctgatgg cataggcccc   12120
tttggaaggg gtagtgtgag tctcttgggg ctatggcaag caccctgga  caagcaggaa   12180 gagaggtggt ggaggcatgt ctcacggtag catctccttc taggtcctaa tgggacactt   12240
cattaatgga actaccattt aagtgagttt aaactggatg cttctgattg agccccagag   12300
ccagtgctcc actgccacca cctgcaccct cacttcccct tgtttaagca tcttccaacc   12360
cagtaaggct gaagagggaa gcatcctgcc ttcccacttc tcttagcaga gtagattgat   12420
atgattattc agattgtaca agaatctatt ccctctgaag tattgcttga tgaatgagcc   12480
cctttttcta atttgctcaa agaaatcatt tgagcttgag gaaaactgtc cagagggcac   12540
gaggaccagc cgttgtgata tgtaacaagg tagagaaaca aaagctaaat gaagaagagt   12600
gagcctcaga atcaaagaac tggatttgga tcccttaaaa ccattttaca ggggcctgaa   12660
tgtaattaac ttctctgaaa ttcagttttcc ttatcaatat gctggtgata agtgactatt   12720
gtttgaagac agcataagca aagcatgcag tacttaggag atgtgttctt ccttcaattc   12780
ctctattatt aaaagatggg cacagggcag gggcttcagc tcagaaggcc ttgttgagaa   12840
tggaatggag agcaggaaca agagagaggg gcaaaggcat tgccagcatt ctctgttcgg   12900
ctgttctcca cccactgcct ttcctcctgc ttccctctaa gtccaggca  ttttcccttt   12960 tgataaactt cccctttttac aacccatcca agggtgaaaa acaaagtcat tacttttttt   13020
tcagtacctc taaggcaaag cagcagaaac aggcagtcac cactacgaat aagtgactac   13080
aacaagagct aggccaaact ctgccatgtg ggctgcattt tattgggccg gcaagtaact   13140
ttaaatccca gctcacactc tactgagtga aagtctgatg aacccgcatc ttcttgtgaa   13200
caactgcgcc tgagatcagt catgcaagaa gtagcacccc caccccaga  caactaactt   13260 cccaggctgt gaccaacaag cagccaagag gccaggacag ggaagtctca ggacctttct   13320
aggaaatcaa tacctttctc tgggtttgtt ctgcctgaaa taataccaat ctccctccaa   13380
cagcttagca tgtgtggagc atttgatact aacagcaacc ctgcaaggca ggaaggcagt   13440
agggagaggc ccaagaggaa ttcagcatta aggcagtgag actgacagag ggaccccct   13500 gaggacattc tggaaggtct tagccagggc caggatgcag acccttcatg tcactgtagc   13560
tgagacgagg tgcaaggttc acagcatata acctaatttt attacaagaa taaagactca   13620
gagtttaaat actcctgctt tggggctcat tagtaacaag ttctccaata ttcaaaaggc   13680
aaagtggatg tgttttagtg taaaattaac actagctgct gtaacaaata agccccccaaa   13740 catatgatat ctcaaacacc gtaggtttat ttctcactca catcagagtc aaaatggatg   13800
tttctaacct gcagctgggg cttctcccag cagtattagg ggcactttcc atcttgtggc   13860
```

```
tccaccgtct gtaatgcagg actccaagtg gtggaagagg acggagcaga ggagtcacac   13920
atgggtgtgt gtcctggccca gggtggaagt ggatgtgcat ttcttctgcc cacctcactc   13980
acaaggccac accccactgc aagagaggct ggagaatgcg gactggattt aaacccaaga   14040
agaagaaatg gttttctgaa tagttggcca tttactgaca caaaaagggt caaagtgact   14100
tgcagaggag atgaatttta atactataa ttatttcctt ggctgccctt tagacagaat   14160
ttatttcttt ttcttttcca gttaaacctg aggctccttt tgacctgagt gtcgtctatc   14220
gggaaggagc caatgacttt gtggtgacat ttaatacatc acacttgcaa agaagtatg   14280
taaaagtttt aatgcacgat gtagcttacc gccaggaaaa ggatgaaaac aaatggacgg   14340
tatgtagttc aactacatta ataaaataaa aacttatgaa tgttttctat tttgttggcc   14400
tagtagtgca tttccctgg gagggcccaa caattttgct tcaaaatct accttctact   14460
gaaagaatct cccaatattg gccccatgaa aacctggatc ttccctgatg catactcttc   14520
tagctctggt tgttttcttc tgctctaatt ttggtcttca gaatgttct acattagtga   14580
gttggataac aatatagatt gaggccaaat taatcctctg tattcagggg cctcaaaaag   14640
tgtcatgtct agtgccactt tcataggcaa atcaggcaaa atgtatatct gcttatgatc   14700
accaagtcgt agccacattc tggcttatga gattcatggg accagcatga ggtaaagaaa   14760
agaggcataa tgtttgcctt tgttttgttt ttatttttaaa gcccaaggtc tttgtttttg   14820
aagtaacagc ttaattttta cccttcataa tcaggagagt tacttagatg ctctcttcat   14880
gatttgttga ggttggaatg atttggcagt ccctgaaatt tatttgggg aggaggtggc   14940
agaagagtgg agtgtaccag gttatgagat ttctcttaac ccaccaacct aacttctgtt   15000
ctttctgcac ctcagagatg aagaagagat gatgatttct cttcctcaag tccttcttat   15060
tcttgctgtc ctgttttttc aggccaagat tggccttgtt tgtttgcagt gtgatgcaag   15120
atgccacttg cataaatgta acaactgccc caaaccacct gctccctcct tctactcacc   15180
caccccaccc ttgatcctgc catctttcat tattcatctg aaaattgcac caattgaaaa   15240
gcaacttagt ggagaaagga aggattatga ataaatgctg ccaggacaat tagttaacta   15300
aaaagaaaaa tagataaatt caataaatac atgaattttt ttgagatgga gtcttgctca   15360
gtcatccagg ttggagtgca atggcgccat cttggctcac tgcaacctcc gcctcccggg   15420
ttcaagcaat tctcccatct cagcctccca agtacctgtg attacaggca cccgccatca   15480
tgcccggcta attttttgtat ttttgtagag ctggggtttc accatgttgg ccaggctggt   15540
cttgaactcc tcacctcagg tgatctgccc acctcagcct cccaaagtgc tgggattaca   15600
ggcataagcc aacacgccag ccaaaaattg ttttaattaa aaaaaattaa actaaatgcc   15660
tagccacctt catataacaa caacaaaata ccagatgatt taaggaaatt atataaaagt   15720
gaaactctaa acaaattaga aaaattatag ccaaatgttt acataatctt gacatgaaga   15780
agaacattct aagcatcaaa gctgtagaag aaaagaaagg attgagacat gcaactacat   15840
aaaaagtgga ggtttatata tgtcaacaca cacaataatc aaaaatcaaa aatgcaaatt   15900
taaaagtaag cttaaattgc cacataaaca gctgatagat ggttagtatc attaatagat   15960
aaaggactct tataaatcat taaaaaaaca aatatcacaa tagaaaaatg agcaaaaaaa   16020
ttgggaaaaa tctcataaag tatggaatag ataaattcaa taaatatatg aaaatgaact   16080
aattatcaaa taaatacaga tataaatagc aatggacttc ttttatctg tcaaattgat   16140
agagtggttt ttttttaatc ttaaagataa tacactgtgt ggtggagact tttgtctctt   16200
tatcactatt cacaatgtaa aatggcgtct ttctggagag aaatgattcc tgctcactaa   16260
```

```
cctaacctaa cctttcatct ccccttaata tgtgaaagga tagagagaaa agaagaagat    16320
attgaagtgt ggaaagggag atcctgggca gtgcctaact cacctgaata agacccatca    16380
tttcactctc ctccttgacc actcacaaca tcctttataa gctcagattc tgtccctaat    16440
tttgctgttg actcctttac gtatcagagc tccttattct aacaaatacg agacaacttc    16500
agagaatgct tatgggacta aaggaatccc aattgaaatg atttgggaga tttaggcaac    16560
acctcttttc ccatcctaag aatgtaactg cactctactc tctagcatgt gaatttatcc    16620
agcacaaagc tgacactcct gcagagaaag ctccaaccgg cagcaatgta tgagattaaa    16680
gttcgatcca tccctgatca ctattttaaa ggcttctgga gtgaatggag tccaagttat    16740
tacttcagaa ctccagagat caataatagc tcaggtaagg aatggtggta gagttttttgt   16800 tccctcagag tgctttgcat gtcaaagtgt gggagcaagt gagaggaaga ttgttgaaac    16860
taacctgcaa aataggacac ccttggaggg cactcttaca ctttctttgg agaatgactt    16920
gcctgctgtc tttgcgcctt ttgtgaagaa caaggaagca gagggagtgg ggtccttatt    16980
agctgagaat tagtacaagc catctgtatt cctggaagct gccatacatt ttgaacaaaa    17040
tccccaccca ctacgtccag ttaaccaatt tagcctggga ccccaatggc tgctgtctct    17100
aaggcccctt taagaagcac ctttattggt gtcaggtatg caggcaagtg cggctgtcct    17160
atgtctcctt ttccagaagg atgaagatgt ctttgggact ggaactgaga atgtgtagga    17220
actgagacat ctcctcccta aaatttgcaa cagggggtgaa catccctctc atcatctcct    17280
gctctggctt cttttccttg gtagaaagtc aagaagggaa gagagcattg gtacctttga    17340
tgctagatca cgtttacatt tcaagtggca gatgctctgg gcctggtcac ccaagtcaat    17400
gccttttaaa ccaaaatccc tccataaagc tgtcaaatat gtctcttaac tgaaaagcaa    17460
ctttcaggaa ataataagtg ggcccacatt actaagtaaa tgcaaagcac cctgagaccc    17520 taccccacact gcatggctac tgaatgctca ccacaatcta ttcttgcttt ccaggggaga    17580
tggatcctat cttactaacc atcagcattt tgagtttttt ctctgtcgct ctgttggtca    17640
tcttggcctg tgtgttatgg aaaaaaaggt gaccttcttc aactaataaa gagggtgatt    17700
gtgtgggatc acgacagtc agagcttaag ccccatttat tgatgagaaa accacaaagg     17760
ggattaaggc atttcacgaa tttagtgccc agtatcccta tctatcctca gcgaatttcc    17820
acagttaatt tcataagagg caaaaagata ttaactggac attaggcaaa cgctgtcccc    17880
aaagtaagaa ttccgtaatg caatgtttcc caagcttttc ttccagtatc tcctaaaggt    17940
tgcagaagcc atcattcatg gcaaatgcac aatgtacttg aagtcttgac tttaagcata    18000
taaattcatg ggattttta tactaatcca tgctaaggct atgtttgttt catcataaaa     18060
atgatgtttt aaacatgcac ttgttaaatt acttactatt ctaggagaat gcccttggca    18120
gaaggctaca tatccccagg attacaaata ccctaatttg aaaagtactg cctggaaagt    18180
actaagcaat ttccctgggt aatttgaaaa tattccccca cttccaccaa aattagctgc    18240
cagagttgct gtcagtaaag agaagaaata aaaagacaac acttaaattg ggagtaaaca    18300
acggggttaa atttacttcc atagctgcac caaaattacc tccttgcaag ccttggtgtt    18360
ccttccctct agggcttttt cccagaggta tattattgtc atgtcttgtt cacagaatgg    18420
attgatatct gtggtctctg gtccaacccc tccttgaatt gatagggccc cgaggcccag    18480
agaaagccag tctcttgacc atggtcaccc acctaattgt gttagagcca agactagaaa    18540
tctgttcttc tgattccaag ctcagaataa gtgggaagac tcagtgtgcc tgtgccctct    18600
```

```
gccattcact tcatctatca atgttctctg atttcaggat taagcctatc gtatggccca    18660
gtctccccga tcataagaag actctggaac atctttgtaa gaaaccaaga aaagtgagtg    18720 ttttggtgc ttaaaaagtg ttgtgttggc aacatcccag tggccaagaa tgatattcca     18780
ggacaaggaa cagttgaacc tcaccttttg gtatttgatt catcctgtaa ctagggtccc    18840
tcctaagacc ctagctgcag tagggaactg aaataagata cacatctcag aacttctggg    18900
ctccctgggg ctggagggca cagccagtgg tcacttcaag tcttgaagtg tctcagaagc    18960
tccagaagca aagagtccat tgaggaacat gctggcaatt ctgtgacatt ccctgtcaga    19020
aaactctata gacctactcc tgaactgaac atttgatggt gtgtctctct ggtgccatct    19080 taatacccctt tctccttttt ctgtgcagaa tttaaatgtg agtttcaatc ctgaaagttt    19140
cctggactgc cagattcata gggtggatga cattcaagct agagatgaag tggaaggttt    19200
tctgcaagat acgtttcctc agcaactaga agaatctgag aagcagaggc ttggagggga    19260
tgtgcagagc cccaactgcc catctgagga tgtagtcatc actccagaaa gctttggaag    19320
agattcatcc ctcacatgcc tggctgggaa tgtcagtgca tgtgacgccc ctattctctc    19380
ctcttccagg tccctagact gcagggagag tggcaagaat gggcctcatg tgtaccagga    19440
cctcctgctt agccttggga ctacaaacag cacgctgccc cctccatttt ctctccaatc    19500
tggaatcctg acattgaacc cagttgctca gggtcagccc attcttactt ccctgggatc    19560
aaatcaagaa gaagcatatg tcaccatgtc cagcttctac caaaaccagt gaagtgtaag    19620
aaacccagac tgaacttacc gtgagcgaca aagatgattt aaaagggaag tctagagttc    19680
ctagtctccc tcacagcaca gagaagacaa aattagcaaa accccactac acagtctgca    19740
agattctgaa acattgcttt gaccactctt cctgagttca gtggcactca acatgagtca    19800
agagcatcct gcttctacca tgtggatttg gtcacaaggt ttaaggtgac ccaatgattc    19860
agctatttaa aaaaaaaga ggaaagaatg aaagagtaaa ggaaatgatt gaggagtgag    19920
gaaggcagga agagagcatg agaggaaaga aagaaaggaa aataaaaaat gatagttgcc    19980
attattagga tttaatatat atccagtgct ttgcaagtgc tctgcgcacc ttgtctcact    20040
ccatcctgac aataatcctg ggaggtgtgt gcaattacta cgactactct cttttttata    20100
gatcattaaa ttcagaacta aggagttaag taacttgtcc aagttgttca cacagtgaag    20160 ggagggggcca agatatgatg gctgggagtc taattgcagt tccctgagcc atgtgccttt    20220
ctcttcactg aggactgccc cattcttgag tgccaaacgt cactagtaac agggtgtgcc    20280
tagataattt atgatccaaa ctgagtcagt ttggaaagtg aaagggaaac ttacatataa    20340
tccctccggg acaatgagca aaaactagga ctgtccccag acaaatgtga acatacatat    20400
catcacttaa attaaaatgg ctatgagaaa gaaagagggg gagaaacagt cttgcgggtg    20460
tgaagtccca tgaccagcca tgtcaaaaga aggtaaagaa gtcaagaaaa agccatgaag    20520
cccatttggt ttcatttttc tgaaaatagg ctcaagaggg aataaattag aaactcacaa    20580
tttctcttgt ttgttaccaa gacagtgatt ctcttgctgc taccacccaa ctgcatccgt    20640
ccatgatctc agaggaaact gtcgctgacc ctggacatgg gtacgtttga cgagtgagag    20700
gaggcatgac ccctcccatg tgtatagaca ctacccccaac ctaaattcat ccctaaattg    20760
tcccaagttc tccagcaata gaggctgcca caaacttcag ggagaaagag ttacaagtac    20820
atgcaatgag tgaactgact gtggctacaa tcttgaagat atacggaaga gacgtattat    20880
taatgcttga catatatcat cttgcctttc ttggtctaga ctgacttcta atgactaact    20940
caaagtcaag gcaactgagt aatgtcagct cagcaaagtg cagcaaaccc atctcccaca    21000
```

```
ggcctccaaa ccctggctgt tcacagaacc acaaagggca gatgctgcac agaaaactag    21060 agaagggggtc ataggttcat ggttttgttt gagatttgtt gctactgttt ttctgttttg    21120
aattttcttc tttgttctgt ttttacttta tttaggggga ctaggtgttt ctgatatttt    21180
agttttcttg tttgttttgt tttgtgttgt ctgtgaatgg ggttttaact gtggatgaat    21240
ggaccttatc tgttggctta aaggactggt aagatcagac catcttattc ttcaggtgaa    21300
tgttttactt tccaaagtgc tctcctctgc accagcagta ataaatacaa tgccataatc    21360
ccttaggttt gcctagtgct tttgcaattt tcaaagcact tccataagca ttccttccac    21420
ctccttgata ggcatttatg gaaagcctgc tacatgtcaa tcatactgtt aggcacaggg    21480
gacctaaaga cacataaaag gatggcattc tgcctcataa attgcaaaac ctaatgaaag    21540
tgactgcttg gtaaacaaat tattattata ttataaaatg ctataaaaga gccatattga    21600
aagtgccctg ttggagacag ggcaaatgcc acaaaaatga tgtaaattta catggaggaa    21660
aagtagaatc tgcctggttt gtaggcagca gaagacattt ttcatcagtg ggcaggtgtt    21720
ctttaccttt tgtagaaatg ggagtcaagt ctcaaatagg aggctccaca aaatctcatg    21780
ccaggtctct gataccttat tcacagaagt tctttgaagt atttattgtt attttctttg    21840
acttatggga aaactgggac acaggaagac aggtaaatta cccaacctca cacgttaagt    21900
cagaactggg agccataatt ttgtatccct ggtataaata dacaatctct tgaagaaatg    21960
aagagatgac catagaaaaa catcgagata tctccagctc taaaatcctt tgtttcaatg    22020
ttgtttggca tatgttatct ttggaattta gtgtctgagc ctctgtctgt tactgtagta    22080
tttaaaatgc atgtattata atcatataat cataactgct gttaattctt gattatatac    22140
ctagggacaa tgtgtaatgt aagattacta attggttctg cccaatctcc tttcagattt    22200
tattaggaaa aaaaataaaa cctcctgatc ggagacaatg tattaatcag aagtgtaaac    22260
tgccagttct atatagcatg aaatgaaaag acagctaatt tggtccaaca aacatgactg    22320
ggtctagggc acccaggctg attcagctga tttcctacca gcctttgcct cttccttcaa    22380
tgtggtttcc atgggaattt gcttcagaaa agccaagtat gggctgttca gaggtgcaca    22440
cctgcatttt cttagctctt ctagaggggc taagagactt ggtacgggcc aggaagaata    22500
tgtggcagag ctcctggaaa tgatgcagat taggtggcat ttttgtcagc tctgtggttt    22560
attgttggga ctattcttta aaatatccat tgttcactac agtgaagatc tctgatttaa    22620
ccgtgtacta tccacatgca ttacaaacat ttcgcagagc tgcttagtat ataagcgtac    22680
aatgtatgta ataaccatct catatttaat taaatggtat agaagaaca        22729
```

<210> SEQ ID NO 2
<211> LENGTH: 4626
<212> TYPE: RNA
<213> ORGANISM: Artificial Sequence
<220> FEATURE:
<223> OTHER INFORMATION: IL7R-001 transcript
<400> SEQUENCE: 2

```
gtggttagat aagtataaag ccctagatct aagcttctct gtcttcctcc ctccctccct     60
tcctcttact ctcattcatt tcatacacac tggctcacac atctactctc tctctctatc    120
tctctcagaa tgacaattct aggtacaact tttggcatgg ttttttcttt acttcaagtc    180
gtttctggag aaagtggcta tgctcaaaat ggagacttgg aagatgcaga actggatgac    240
tactcattct catgctatag ccagttggaa gtgaatggat cgcagcactc actgacctgt    300
```

```
gcttttgagg acccagatgt caacatcacc aatctggaat ttgaaatatg tggggccctc    360
gtggaggtaa agtgcctgaa tttcaggaaa ctacaagaga tatatttcat cgagacaaag    420
aaattcttac tgattggaaa gagcaatata tgtgtgaagg ttggagaaaa gagtctaacc    480
tgcaaaaaaa tagacctaac cactatagtt aaacctgagg ctccttttga cctgagtgtc    540
gtctatcggg aaggagccaa tgactttgtg gtgacattta atacatcaca cttgcaaaag    600
aagtatgtaa aagttttaat gcacgatgta gcttaccgcc aggaaaagga tgaaaacaaa    660
tggacgcatg tgaatttatc cagcacaaag ctgacactcc tgcagagaaa gctccaaccg    720
gcagcaatgt atgagattaa agttcgatcc atccctgatc actattttaa aggcttctgg    780
agtgaatgga gtccaagtta ttacttcaga actccagaga tcaataatag ctcaggggag    840
atggatccta tcttactaac catcagcatt ttgagttttt tctctgtcgc tctgttggtc    900
atcttggcct gtgtgttatg gaaaaaaagg attaagccta tcgtatggcc cagtctcccc    960
gatcataaga agactctgga acatctttgt aagaaaccaa gaaaaatttt aaatgtgagt   1020
ttcaatcctg aaagtttcct ggactgccag attcataggg tggatgacat tcaagctaga   1080
gatgaagtgg aaggttttct gcaagatacg tttcctcagc aactagaaga atctgagaag   1140
cagaggcttg gagggatgt gcagagcccc aactgcccat ctgaggatgt agtcatcact   1200
ccagaaagct ttggaagaga ttcatccctc acatgcctgg ctgggaatgt cagtgcatgt   1260
gacgccccta ttctctcctc ttccaggtcc ctagactgca gggagagtgg caagaatggg   1320
cctcatgtgt accaggacct cctgcttagc cttgggacta caaacagcac gctgccccct   1380
ccattttctc tccaatctgg aatcctgaca ttgaacccag ttgctcaggg tcagcccatt   1440
cttacttccc tgggatcaaa tcaagaagaa gcatatgtca ccatgtccag cttctaccaa   1500
aaccagtgaa gtgtaagaaa cccagactga acttaccgtg agcgacaaag atgatttaaa   1560
agggaagtct agagttccta gtctccctca cagcacagag aagacaaaat tagcaaaacc   1620
ccactacaca gtctgcaaga ttctgaaaca ttgctttgac cactcttcct gagttcagtg   1680
gcactcaaca tgagtcaaga gcatcctgct tctaccatgt ggatttggtc acaaggttta   1740
aggtgaccca atgattcagc tatttaaaaa aaaaagagga aagaatgaaa gagtaaagga   1800
aatgattgag gagtgaggaa ggcaggaaga gagcatgaga ggaaagaaag aaaggaaaat   1860
aaaaaatgat agttgccatt attaggattt aatatatatc cagtgctttg caagtgctct   1920
gcgcaccttg tctcactcca tcctgacaat aatcctggga ggtgtgtgca attactacga   1980
ctactctctt ttttatagat cattaaattc agaactaagg agttaagtaa cttgtccaag   2040
ttgttcacac agtgaaggga ggggccaaga tatgatggct gggagtctaa ttgcagttcc   2100
ctgagccatg tgcctttctc ttcactgagg actgccccat tcttgagtgc aaacgtcac   2160 tagtaacagg gtgtgcctag ataatttatg atccaaactg agtcagtttg gaaagtgaaa   2220
gggaaactta catataatcc ctccgggaca atgagcaaaa actaggactg tccccagaca   2280
aatgtgaaca tacatatcat cacttaaatt aaaatggcta tgaaagaa agaggggag    2340 aaacagtctt gcgggtgtga agtcccatga ccagccatgt caaaagaagg taaagaagtc   2400
aagaaaaagc catgaagccc atttggtttc atttttctga aaataggctc aagagggaat   2460
aaattagaaa ctcacaattt ctcttgtttg ttaccaagac agtgattctc ttgctgctac   2520
cacccaactg catccgtcca tgatctcaga ggaaactgtc gctgaccctg gacatgggta   2580
cgtttgacga gtgagaggag gcatgacccc tcccatgtgt atagacacta ccccaaccta   2640
aattcatccc taaattgtcc caagttctcc agcaatagag gctgccacaa acttcaggga   2700
```

-continued

```
gaaagagtta caagtacatg caatgagtga actgactgtg gctacaatct tgaagatata    2760
cggaagagac gtattattaa tgcttgacat atatcatctt gcctttcttg gtctagactg    2820
acttctaatg actaactcaa agtcaaggca actgagtaat gtcagctcag caaagtgcag    2880
caaacccatc tcccacaggc ctccaaaccc tggctgttca cagaaccaca aagggcagat    2940
gctgcacaga aaactagaga aggggtcata ggttcatggt tttgtttgag atttgttgct    3000
actgtttttc tgttttgaat tttcttcttt gttctgtttt tactttatttt aggggacta    3060 ggtgtttctg atattttagt tttcttgttt gttttgtttt gtgttgtctg tgaatggggt    3120
tttaactgtg gatgaatgga ccttatctgt tggcttaaag gactggtaag atcagaccat    3180
cttattcttc aggtgaatgt tttactttcc aaagtgctct cctctgcacc agcagtaata    3240
aatacaatgc cataatccct taggtttgcc tagtgctttt gcaattttca aagcacttcc    3300
ataagcattc cttccacctc cttgataggc atttatggaa agcctgctac atgtcaatca    3360
tactgttagg cacaggggac ctaaagacac ataaaaggat ggcattctgc ctcataaatt    3420 gcaaaccta atgaaagtga ctgcttggta acaaattat tattatatta taaaatgcta     3480
taaaagagcc atattgaaag tgccctgttg gagacagggc aaatgccaca aaaatgatgt    3540
aaatttacat ggaggaaaag tagaatctgc ctggtttgta ggcagcagaa gacatttttc    3600
atcagtgggc aggtgttctt tacctttgt agaaatggga gtcaagtctc aaataggagg     3660
ctccacaaaa tctcatgcca ggtctctgat accttattca cagaagttct tgaagtatt     3720 tattgttatt ttctttgact tatgggaaaa ctgggacaca ggaagacagg taaattaccc    3780
aacctcacac gttaagtcag aactgggagc cataatttg tatccctggt ataaatagac     3840
aatctcttga agaaatgaag agatgaccat agaaaaacat cgagatatct ccagctctaa    3900
aatcctttgt ttcaatgttg tttggcatat gttatctttg gaatttagtg tctgagcctc    3960
tgtctgttac tgtagtattt aaaatgcatg tattataatc atataatcat aactgctgtt    4020
aattcttgat tatataccta gggacaatgt gtaatgtaag attactaatt ggttctgccc    4080
aatctccttt cagattttat taggaaaaaa aaataaacct cctgatcgga gacaatgtat    4140
taatcagaag tgtaaactgc cagttctata tagcatgaaa tgaaaagaca gctaatttgg    4200
tccaacaaac atgactgggt ctagggcacc caggctgatt cagctgattt cctaccagcc    4260
tttgcctctt ccttcaatgt ggtttccatg ggaatttgct tcagaaaagc caagtatggg    4320
ctgttcagag gtgcacacct gcattttctt agctcttcta gaggggctaa gagacttggt    4380
acgggccagg aagaatatgt ggcagagctc ctggaaatga tgcagattag gtggcatttt    4440
tgtcagctct gtggtttatt gttgggacta ttctttaaaa tatccattgt tcactacagt    4500
gaagatctct gatttaaccg tgtactatcc acatgcatta caaacatttc gcagagctgc    4560
ttagtatata agcgtacaat gtatgtaata accatctcat atttaattaa atggtataga    4620
agaaca                                                               4626
```

<210> SEQ ID NO 3
<211> LENGTH: 1287
<212> TYPE: RNA
<213> ORGANISM: Artificial Sequence
<220> FEATURE:
<223> OTHER INFORMATION: IL7R-002 transcript

<400> SEQUENCE: 3

```
gtcttcctcc ctccctccct tcctcttact ctcattcatt tcatacacac tggctcacac       60
```

| | |
|---|---|
| atctactctc tctctctatc tctctcagaa tgacaattct aggtacaact tttggcatgg | 120 |
| ttttttcttt acttcaagtc gtttctggag aaagtggcta tgctcaaaat ggagacttgg | 180 |
| aagatgcaga actggatgac tactcattct catgctatag ccagttggaa gtgaatggat | 240 |
| cgcagcactc actgacctgt gcttttgagg acccagatgt caacatcacc aatctggaat | 300 |
| ttgaaatatg tggggccctc gtggaggtaa agtgcctgaa tttcaggaaa ctacaagaga | 360 |
| tatatttcat cgagacaaag aaattcttac tgattggaaa gagcaatata tgtgtgaagg | 420 |
| ttggagaaaa gagtctaacc tgcaaaaaaa tagacctaac cactatagtt aaacctgagg | 480 |
| ctccttttga cctgagtgtc gtctatcggg aaggagccaa tgactttgtg gtgacattta | 540 |
| atacatcaca cttgcaaaag aagtatgtaa agtttttaat gcacgatgta gcttaccgcc | 600 |
| aggaaaagga tgaaaacaaa tggacggatt aagcctatcg tatggcccag tctccccgat | 660 |
| cataagaaga ctctggaaca tctttgtaag aaaccaagaa aaaatttaaa tgtgagtttc | 720 |
| aatcctgaaa gtttcctgga ctgccagatt catagggtgg atgacattca agctagagat | 780 |
| gaagtggaag gttttctgca agatacgttt cctcagcaac tagaagaatc tgagaagcag | 840 |
| aggcttggag gggatgtgca gagccccaac tgcccatctg aggatgtagt catcactcca | 900 |
| gaaagctttg aagagattc atccctcaca tgcctggctg ggaatgtcag tgcatgtgac | 960 |
| gcccctattc tctcctcttc caggtcccta gactgcaggg agagtggcaa gaatgggcct | 1020 |
| catgtgtacc aggacctcct gcttagcctt gggactacaa cagcacgct gcccctcca | 1080 |
| ttttctctcc aatctggaat cctgacattg aacccagttg ctcagggtca gcccattctt | 1140 |
| acttccctgg gatcaaatca agaagaagca tatgtcacca tgtccagctt ctaccaaaac | 1200 |
| cagtgaagtg taagaaaccc agactgaact taccgtgagc gacaaagatg atttaaaagg | 1260 |
| gaagtctaga gttcctagtc tccctca | 1287 |

<210> SEQ ID NO 4
<211> LENGTH: 1004
<212> TYPE: RNA
<213> ORGANISM: Artificial Sequence
<220> FEATURE:
<223> OTHER INFORMATION: IL7R-003 transcript

<400> SEQUENCE: 4

| | |
|---|---|
| cttcctccct ccctcccttc ctcttactct cattcatttc atacacactg gctcacacat | 60 |
| ctactctctc tctctatctc tctcagaatg acaattctag gtacaactt tggcatggtt | 120 |
| ttttctttac ttcaagtcgt ttctggagaa agtggctatg ctcaaaatgg agacttggaa | 180 |
| gatgcagaac tggatgacta ctcattctca tgctatagcc agttggaagt gaatggatcg | 240 |
| cagcactcac tgacctgtgc ttttgaggac ccagatgtca acatcaccaa tctggaattt | 300 |
| gaaatatgtg ggccctcgt ggaggtaaag tgcctgaatt tcaggaaact acaagagata | 360 |
| tatttcatcg agacaaagaa attcttactg attggaaaga gcaatatatg tgtgaaggtt | 420 |
| ggagaaaaga gtctaacctg caaaaaaata gacctaacca ctatagttaa acctgaggct | 480 |
| ccttttgacc tgagtgtcgt ctatcgggaa ggagccaatg actttgtggt gacatttaat | 540 |
| acatcacact tgcaaagaa gtatgtaaaa gttttaatgc acgatgtagc ttaccgccag | 600 |
| gaaaaggatg aaaacaaatg gacgcatgtg aatttatcca gcacaaagct gacactcctg | 660 |
| cagagaaagc tccaaccggc agcaatgtat gagattaaag ttcgatccat ccctgatcac | 720 |
| tattttaaag gcttctggag tgaatggagt ccaagttatt acttcagaac tccagagatc | 780 |
| aataatagct caggattaag cctatcgtat ggcccagtct ccccgatcat aagaagactc | 840 |

```
tggaacatct tgtaagaaa ccaagaaaag tgagtgtttt tggtgcttaa aaagtgttgt      900
gttggcaaca tcccagtggc caagaatgat attccaggac aaggaacagt tgaacctcac      960
cttttggtat ttgattcatc ctgtaactag ggtccctcct aaga                     1004
```

<210> SEQ ID NO 5
<211> LENGTH: 562
<212> TYPE: RNA
<213> ORGANISM: Artificial Sequence
<220> FEATURE:
<223> OTHER INFORMATION: IL7R-004 transcript

<400> SEQUENCE: 5

```
aaatgctaga gactattcat ttaggaccag agtggcatta gctttcctac agccatcctc       60
acctgcttga caccttgga tgttgggttt ttttgtttgt ttgtttgttt gtttgttgtt      120
ttttttttcc acagctcttg tggtccccag cctctctctt gagcagggct ggcttttttt      180
ttttaataag atagctggtg cccaagattg ttttccacct taaggataaa acctgttaag      240
aaaggtcata gtttgccagc ccctgcccta acaaataat tcttgaatgc ctactgtggt       300
gtgtaagata tgagtaaata ccagggatac acagagaaca aaagagaaaa actgctattc      360
ttgtgaaact tggaagttgg agaatgacaa ttctaggtac aacttttggc atggtttttt      420
ctttacttca agtcgtttct ggagaaagtg gctatgctca aaatggagac ttggaagatg      480
cagaactgga tgactactca ttctcatgct atagccagtt ggaagtgaat ggatcgcagc      540
actcactgac ctgtgctttt ga                                            562
```

<210> SEQ ID NO 6
<211> LENGTH: 515
<212> TYPE: RNA
<213> ORGANISM: Artificial Sequence
<220> FEATURE:
<223> OTHER INFORMATION: IL7R-005 transcript

<400> SEQUENCE: 6

```
agagtggcat tagctttcct acagccatcc tcacctgctt gacacccttg gatgttgggt       60 tttttgttt gtttgtttgt tgtttgttg ttttttttt ccacagctct tgtggtcccc        120
agcctctctc ttgagcaggg ctggcttttt tttttaata agatagctgg tgcccaagat       180
tgttttccac cttaaggata aaacctgtta agaaaggaga cttggaagat gcagaactgg      240
atgactactc attctcatgc tatagccagt tggaagtgaa tggatcgcag cactcactga      300
cctgtgcttt tgaggaccca gatgtcaaca tcaccaatct ggaatttgaa atatgtgggg      360
ccctcgtgga ggtaaagtgc ctgaatttca ggaaactaca agatatatat ttcatcgaga      420
caaagaaatt cttactgatt ggaaagagca atatatgtgt gaaggttgga gaaaagagtc      480
taacctgcaa aaaatagac ctaaccacta taggt                                515
```

<210> SEQ ID NO 7
<211> LENGTH: 551
<212> TYPE: RNA
<213> ORGANISM: Artificial Sequence
<220> FEATURE:
<223> OTHER INFORMATION: IL7R-006 transcript

<400> SEQUENCE: 7

```
cttttaaagt gggcccttag tcaggagcgg tggctcatgc ctgtagtcct agcactttgg       60
gaggctgagg caggcagatc acttgaggtc aggagttcga gacaagcctg gccaacatgg      120
```

```
cgaaaccccg tctccactga aaacacaaaa attaggctgg catagtggca tttgcctgta    180
gtcctagcta ctcaggaggc tgaggcagga gaattgcttg aacctgggag gtggaaattg    240
cagtgagccg agatcatgct attgtactcc agcctgggca acaaagcaag actctgtctc    300
aaaaaaataa aaattaaaaa aataaagtag cctctagcct aagatagctt gagcctaggt    360
gtgaatctac tgccttactc tgatgtaagc acaaatgaca attctaggta caacttttgg    420
catggttttt tctttacttc aagtcgtttc tggagaaagt ggctatgctc aaaatggaga    480
cttggaagat gcagaactgg atgactactc attctcatgc tatagccagt tggaagtgaa    540
tggatcgcag c                                                        551

<210> SEQ ID NO 8
<211> LENGTH: 612
<212> TYPE: RNA
<213> ORGANISM: Artificial Sequence
<220> FEATURE:
<223> OTHER INFORMATION: IL7R-007 transcript

<400> SEQUENCE: 8
ttcctccctc cctcccttcc tcttactctc attcatttca tacacactgg ctcacacatc     60
tactctctct ctctatctct ctcagaatga caattctagg tacaacttttt ggcatggttt    120 tttctttact tcaagtcgtt tctggagaaa gtggctatgc tcaaaatgga gacttggaag    180
atgcagaact ggatgactac tcattctcat gctatagcca gttggaagtg aatggatcgc    240
agcactcact gacctgtgct tttgaggacc agatgtcaa catcaccaat ctggaatttg    300
aaatatgtgg ggccctcgtg gaggtaaagt gcctgaattt caggaaacta caagagatat    360
atttcatcga gacaaagaaa ttcttactga ttggaaagag caatatatgt gtgaaggttg    420
gagaaaagag tctaacctgc aaaaaaatag acctaaccac tataggtaag aagttgtata    480
taaaagtatg gttgtcactt ttgggctacc tgaaaacact gtgtctggac attctgtagg    540
ttaaaagtag acaaatagtg gaaacaactg gcaatagata atagctaatt ccctactgta    600
aatttttata at                                                       612

<210> SEQ ID NO 9
<211> LENGTH: 552
<212> TYPE: RNA
<213> ORGANISM: Artificial Sequence
<220> FEATURE:
<223> OTHER INFORMATION: IL7R-008 transcript

<400> SEQUENCE: 9
gtgtggaaag ggagatcctg ggcagtgcct aactcacctg aataagaccc atcatttcac     60
tctcctcctt gaccactcac aacatccttt ataagctcag attctgtccc taattttgct    120
gttgactcct ttacgtatca gagctcctta ttctaacaaa tacgagacaa cttcagagaa    180
tgcttatggg actaaaggaa tcccaattga aatgatttgg gagatttagg caacacctct    240
tttcccatcc taagaatgta actgcactct actctctagc atgtgaattt atccagcaca    300
aagctgacac tcctgcagag aaagctccaa ccggcagcaa tgtatgagat taaagttcga    360
tccatccctg atcactattt taaaggcttc tggagtgaat ggagtccaag ttattacttc    420
agaactccag agatcaataa tagctcaggg gagatggatc ctatcttact aaccatcagc    480
attttgagtt ttttctctgt cgctctgttg gtcatcttgg cctgtgtgtt atggaaaaaa    540
aggattaagc ct                                                       552
```

<210> SEQ ID NO 10
<211> LENGTH: 626
<212> TYPE: RNA
<213> ORGANISM: Artificial Sequence
<220> FEATURE:
<223> OTHER INFORMATION: IL7R-009 transcript

<400> SEQUENCE: 10

```
atctgttctt ctgattccaa gctcagaata agtgggaaga ctcagtgtgc ctgtgccctc      60
tgccattcac ttcatctatc aatgttctct gatttcagga ttaagcctat cgtatggccc     120
agtctccccg atcataagaa gactctggaa catctttgta agaaaccaag aaaaaattta     180
aatgtgagtt tcaatcctga agtttcctg gactgccaga ttcatagggt ggatgacatt      240
caagctagag atgaagtgga aggttttctg caagatacgt ttcctcagca actagaagaa     300
tctgagaagc agaggcttgg aggggatgtg cagagcccca actgcccatc tgaggatgta     360
gtcatcactc cagaaagctt tggaagagat tcatccctca catgcctggc tgggaatgtc     420
agtgcatgtg acgcccctat tctctcctct tccaggtccc tagactgcag ggagagtggc     480
aagaatgggc tcatgtgta ccaggacctc ctgcttagcc ttgggactac aaacagcacg      540
ctgcccctc catttctctct ccaatctgga atcctgacat tgaacccagt tgctcagggt     600
cagcccattc ttacttccct gggatc                                           626
```

<210> SEQ ID NO 11
<211> LENGTH: 917
<212> TYPE: RNA
<213> ORGANISM: Artificial Sequence
<220> FEATURE:
<223> OTHER INFORMATION: IL7R-010 transcript

<400> SEQUENCE: 11

```
gcagcaatgt atgagattaa agttcgatcc atccctgatc actattttaa aggcttctgg      60
agtgaatgga gtccaagtta ttacttcaga actccagaga tcaataatag ctcaggatta     120
agcctatcgt atggcccagt ctccccgatc ataagaagac tctggaacat ctttgtaaga     180
aaccaagaaa aaatttaaat gtgagtttca atcctgaaag tttcctggac tgccagattc     240
ataggggtgga tgacattcaa gctagagatg aagtggaagg ttttctgcaa gatacgtttc     300
ctcagcaact agaagaatct gagaagcaga ggcttggagg ggatgtgcag agccccaact     360
gcccatctga ggatgtagtc atcactccag aaagctttgg aagagattca tccctcacat     420
gcctggctgg gaatgtcagt gcatgtgacg cccctattct ctcctcttcc aggtccctag     480
actgcaggga gagtggcaag aatgggcctc atgtgtacca ggacctcctg cttagccttg     540
ggactacaaa cagcacgctg cccctccat tttctctcca atctggaatc ctgacattga      600
acccagttgc tcagggtcag cccattctta cttccctggg atcaaatcaa gaagaagcat     660
atgtcaccat gtccagcttc taccaaaacc agtgaagtgt aagaaaccca gactgaactt     720
accgtgagcg acaaagatga tttaaaaggg aagtctagaa ttcctagtct ccctcacagc     780
acagagaaga caaaattagc aaaacccac tacacagtct gcaagattct gaaacattgc      840
tttgaccact cttcctgagt tcagtggcac tcaacatgag tcaagagcat cctgcttcta     900
ccatgtggat ttggtca                                                     917
```

<210> SEQ ID NO 12
<211> LENGTH: 20
<212> TYPE: DNA
<213> ORGANISM: Artificial Sequence
<220> FEATURE:

```
<223> OTHER INFORMATION: Forward primer for PCR-A

<400> SEQUENCE: 12
ggaagtgaat ggatcgcagc                                              20

<210> SEQ ID NO 13
<211> LENGTH: 19
<212> TYPE: DNA
<213> ORGANISM: Artificial Sequence
<220> FEATURE:
<223> OTHER INFORMATION: Reverse primer for PCR-A

<400> SEQUENCE: 13
ggcactttac ctccacgag                                               19

<210> SEQ ID NO 14
<211> LENGTH: 22
<212> TYPE: DNA
<213> ORGANISM: Artificial Sequence
<220> FEATURE:
<223> OTHER INFORMATION: Probe for PCR-A

<400> SEQUENCE: 14
ctgtgctttt gaggacccag at                                           22

<210> SEQ ID NO 15
<211> LENGTH: 19
<212> TYPE: DNA
<213> ORGANISM: Artificial Sequence
<220> FEATURE:
<223> OTHER INFORMATION: Forward primer for PCR-B

<400> SEQUENCE: 15
ctctgtcgct ctgttggtc                                               19

<210> SEQ ID NO 16
<211> LENGTH: 21
<212> TYPE: DNA
<213> ORGANISM: Artificial Sequence
<220> FEATURE:
<223> OTHER INFORMATION: Reverse primer for PCR-B

<400> SEQUENCE: 16
tccagagtct tcttatgatc g                                            21

<210> SEQ ID NO 17
<211> LENGTH: 21
<212> TYPE: DNA
<213> ORGANISM: Artificial Sequence
<220> FEATURE:
<223> OTHER INFORMATION: Probe for PCR-B

<400> SEQUENCE: 17
ctatcgtatg gcccagtctc c                                            21

<210> SEQ ID NO 18
<211> LENGTH: 20
<212> TYPE: DNA
<213> ORGANISM: Artificial Sequence
<220> FEATURE:
<223> OTHER INFORMATION: Forward primer for PCR-C

<400> SEQUENCE: 18
ggaagtgaat ggatcgcagc                                              20
```

```
<210> SEQ ID NO 19
<211> LENGTH: 20
<212> TYPE: DNA
<213> ORGANISM: Artificial Sequence
<220> FEATURE:
<223> OTHER INFORMATION: Reverse primer for PCR-C

<400> SEQUENCE: 19
cagaatgtcc agacacagtg                                              20

<210> SEQ ID NO 20
<211> LENGTH: 22
<212> TYPE: DNA
<213> ORGANISM: Artificial Sequence
<220> FEATURE:
<223> OTHER INFORMATION: Probe for PCR-C

<400> SEQUENCE: 20
ctgtgctttt gaggacccag at                                           22
```

KIT FOR ASSESSING THE RISK OF COMPLICATIONS IN PATIENTS WITH SYSTEMIC INFLAMMATORY RESPONSE SYNDROME (SIRS)

This is a divisional application of U.S. patent application Ser. No. 15/780,573, filed May 31, 2018, which is a national phase application of International application number PCT/FR2016/053164, filed Dec. 1, 2016, which claims priority to French patent application number FR 1561671, filed Dec. 1, 2015.

The present invention relates to the medical field in general, and in particular to the field of risk prediction. More precisely, the invention relates to a method of evaluating the risk of complications in a patient having sustained an insult such as surgery, burns, trauma etc., resulting in a systemic inflammatory response syndrome or SIRS, or in a patient suffering from an infection provoking a SIRS, in particular in a patient in a septic state, i.e. a patient presenting a sepsis, in particular severe sepsis, also known as serious sepsis, and preferably a patient in septic shock or who has sustained a septic shock.

With a systemic inflammatory response syndrome or SIRS, both the risk of complications of the secondary infection, or nosocomial infection type in the case of hospitalization, and also the risk of death are high.

Nosocomial infections in particular are a major public health problem. By definition, hospitalized patients often have diminished or damaged immune defenses as a result of pathologies that inflict direct damage on their immunologic competence, or due to their general state. Such patients, and in particular those suffering from malnutrition or in the upper or lower age range (the elderly, infants) are especially sensitive to infections in general, and in particular to the occurrence of nosocomial infections. The incidence of nosocomial infections is markedly higher in intensive care units than in other sections of the hospital.

Furthermore, among systemic inflammatory response syndromes or SIRS, sepsis is a systemic inflammatory response syndrome related to an infection. Severe sepsis is sepsis associated with arterial hypotension and/or hypoperfusion and/or dysfunction of at least one organ. Septic shock is severe sepsis associated with persistent hypotension despite reasonable fluid resuscitation and vasopressor treatments. The difference between sepsis, severe sepsis, and septic shock resides principally in the magnitude of the disruption to all of the vital functions.

Patients presenting with SIRS, and in particular those presenting with septic syndromes, i.e. patients in a septic state ranging from sepsis, severe sepsis, to septic shock, run a high risk of complications, in particular nosocomial infections. In addition, septic states are one of the leading causes of mortality in intensive care services.

Estimating the risk of complications in a patient admitted to an intensive care unit or to other services, for example surgery, in particular major surgery or transplantation, and who presents a SIRS, in particular sepsis, severe sepsis, or in a state of septic shock, is thus essential in order to be able to provide personalized care and thus to attempt to reduce the risk of complications, and in particular of death.

The severity of the condition of a patient admitted into the intensive care unit is generally estimated with the aid of a variety of clinical and physiological parameters. They can in particular be used to define scores that are predictive in terms of survival/mortality; those that may be cited in particular include the following severity scores: SOFA (*Sequential Organ Failure Assessment or Sepsis-related Organ Failure Assessment*) (Vincent et al., 1996); and SAPSII (*Simplified Acute Physiology Score II*) (in French IGS II (Indice de Gravité Simplifié II) [Simplified Gravity Index]) (Le Gall et al., 1993). These composite scores, defined on the basis of substantial cohorts of intensive care patients, include a number of clinical-biological parameters such as the number of circulating platelets, bilirubinemia, diuresis, age, or body temperature. By calculating a numerical value, these scores can be used to evaluate the degree to which the function of one or more physiological systems (for example: cardiovascular, renal, cerebral) is under attack. They are calculated during the first days of admission to intensive care. With the SAPSII score, consideration is given only to the worst value of the parameters included in the score, as measured during the first 24 hours (h) or their stay in intensive care.

However, these scores are of little practical clinical use because they require the physician to carry out an active investigation into the clinical parameters of a patient's history.

Thus, there is a genuine need for the provision of other tools, in particular measurable markers, that can be used readily and rapidly to evaluate the risk of complications and in particular of mortality in a patient admitted into an intensive care unit, who by definition is in a serious condition that could rapidly become life-threatening. Indeed, being able to identify subjects with an increased risk of complications or even of mortality would mean that their care and monitoring as well as therapy could be better tailored to their needs.

Application WO 2013/140103 proposes a method of determining a patient's susceptibility to nosocomial infections, comprising the following steps:
  measuring the expression of sCD127 on a protein level in a biological sample taken from said patient, or "test sample";
  reaching a conclusion as regards increased susceptibility to nosocomial infections after comparing the expression of sCD127 with a reference value.

Application WO 2015/040328, on the other hand, describes a method of evaluating the risk of mortality in a patient who has sustained an insult or an infection generating a systemic inflammatory response or SIRS, comprising the following steps:
  measuring the expression of sCD127 on protein level in a biological sample obtained from said patient, also known as the "test sample",
  reaching a conclusion as regards an increased risk of mortality after comparing the expression of sCD127 with a reference value.

sCD127 is the soluble or plasmatic form of CD127, also known as the alpha chain of the IL-7 receptor or IL-7R-ALPHA or IL-7RA or CDw127 (UniProtKB P16871). CD127 is a 75 kilodalton (kDa) glycoprotein that is a member of the hematopoietic growth factor receptor superfamily. It is expressed at the membrane and becomes associated with CD132 (common $Y_c$ chain) in order to form the IL-7 receptor. This receptor plays an important role in lymphocyte differentiation, survival, and proliferation. CD127 is constituted by an extracellular 219 amino acid (aa) portion, a 25 aa transmembrane portion, and a 195 aa intracytoplasmic portion, (Jiang et al., 2005). Like many cytokine receptors, it has been shown that CD127 can be present in plasma or serum in the soluble form, denoted "sCD127" (Carini et al., 1994; Vranjkovic et al., 2007). The term "sCD127" means the soluble form or circulating form (also known as the plasma or serum form) of the IL-7 receptor. The mechanisms at the origin of the liberation of the soluble form have not been described in detail and the results in the literature are contradictory. Hence, the work by Vranjkovic et al., 2007 concludes that the soluble form originates from cleavage of the membrane form. In contrast, Goodwin et al., 1990 as well as Rose et al., 2009 conclude that regulation of the transcription is via an alternative splicing of the RNA of the IL7R gene coding for CD127.

Application WO 2009/115478, on the other hand, describes an in vitro method of detecting and differentiating a variety of physiopathological states. The detection method described in that document is defined in particular in claim 1 and uses the detection of a number of polynucleotide markers. Various physiopathological states, including SIRS, sepsis, and septic shock are cited. However, it is a question of in vitro detection, differentiation, or observation of past progress, and not of the evaluation of a risk, i.e. a future state. The IL7R gene is cited, among 669 polynucleotides. In the examples (see Tables 10, 11, 13b, 15, 17, 18a and 18b), the markers are used as markers for identifying subjects with SIRS or sepsis, as is clear from Example 3 in particular. Those examples do not in any way concern a method of in vitro or ex vivo evaluation of the risk of complications in a patient who has sustained an insult or infection, but concern the diagnosis of SIRS or sepsis.

The IL7R gene is composed of 8 exons, with exon 6 coding for the transmembrane domain. In particular, the reference nucleic sequence for the gene IL7R is SEQ ID NO: 1 (Ensembl: ENSG00000168685).

A number of transcripts of the IL7R gene exist, collated in the Ensembl (GRCh38.p3) database shown in FIG. 1 and listed in Table 1. The transcript IL7R-001 includes exon 6 and thus corresponds to the membrane protein form of CD127. All of the other transcripts could theoretically lead to translation of a protein not comprising exon 6, and thus potentially correspond to soluble forms of CD127.

TABLE 1

The various transcripts of the IL7R gene according to the Ensembl (GRCh38.p3) database

| Name of transcript | Identification number | SEQ ID NO: | Theoretical protein size | Experimental observation of the protein |
|---|---|---|---|---|
| IL7R-001 | ENST00000303115 NM_002185 | SEQ ID NO: 2 | 459 aa | Yes (Goodwin et al., 1990; Park et al., 1990) |
| IL7R-002 | ENST00000514217 | SEQ ID NO: 3 | 180 aa | No (Rose et al., 2009) |
| IL7R-003 | ENST00000506850 | SEQ ID NO: 4 | 261 aa | Yes (Rose et al., 2009) |
| IL7R-004 | ENST00000508941 | SEQ ID NO: 5 | 59 aa | No |
| IL7R-005 | ENST00000511031 | SEQ ID NO: 6 | Non-coding | No |
| IL7R-006 | ENST00000515665 | SEQ ID NO: 7 | 52 aa | No |
| IL7R-007 | ENST00000511982 | SEQ ID NO: 8 | 150 aa | No |
| IL7R-008 | ENST00000509668 | SEQ ID NO: 9 | Non-coding | No |
| IL7R-009 | ENST00000505875 | SEQ ID NO: 10 | Non-coding | No |
| IL7R-010 | ENST00000505093 | SEQ ID NO: 11 | 65 aa | No |

The study by Rose et al., 2009 in particular was able to show that the sequence for the soluble protein form sCD127 purified from plasma corresponded to the form obtained following translation of the transcript IL7R-003. In that study, the soluble protein did not originate from translation of the transcript IL7R-002, or from cleavage of the membrane protein form.

Until now, soluble protein forms corresponding to transcripts that could potentially be translated, IL7R-002, IL7R-004, IL7R-006, IL7R-007 and IL7R-010, have not been observed experimentally.

In the context of the invention, the inventors of the present patent application propose a method of in vitro or ex vivo evaluation of the risk of complications in a patient who has sustained an insult or an infection, which method adopts a solution other than the detection of soluble proteins, and is based on evaluating one or more transcripts of the IL7R gene. The inventors have demonstrated that in the case of transcripts, it is neither useful nor preferred to be limited to transcripts coding for the soluble portion of CD127, i.e. sCD127.

In this context, then, the present invention proposes supplying a novel biomarker that is predictive of a risk of complications, and in particular of mortality, in a patient who has suffered a severe insult (surgery, burns, trauma, etc.) or infection, said insult or infection generating a systemic inflammatory response syndrome (SIRS). Studying the quantity of one or more transcripts of the IL7R gene can thus be used readily and rapidly to evaluate the risk of complications, and in particular of mortality, in the patient, and to take any possible preventative measures. The invention concerns a method of in vitro or ex vivo evaluation of the risk of complications in a patient who has sustained an insult or an infection, said insult or infection generating a systemic inflammatory response syndrome, in which method at least one transcript of the IL7R gene is detected and preferably quantified in a biological sample obtained from said patient.

In the context of the invention, the term "systemic inflammatory response syndrome" or "SIRS" means a response associating at least two of the following criteria: temperature>38° C. or <36° C., heart rate>90/minute (min), respiratory rate>20/min or $paCO_2$<32 millimeters of mercury (mmHg), leukocytes>12000 per cubic millimeter (/mm$^3$) or <4000/mm$^3$ (Bone et al., 1992). A SIRS may be due to an infection or any other type of insult of the burn, surgery, or trauma type in particular. Sepsis, severe sepsis, and septic shock all correspond to a SIRS due to an infection. In patients in a septic state (sepsis, severe sepsis, and septic shock), which patients therefore present a SIRS as a result of an infection, the infection that caused the SIRS could possibly arise from a variety of origins, and in particular from bacterial, viral, or fungal origins. With severe sepsis and septic shock, the SIRS is accompanied by at least one other manifestation, which, with severe sepsis, is arterial hypotension and/or hypoperfusion and/or dysfunction of at least one organ; in the case of septic shock, this may be supplemented by persistent hypotension despite reasonable fluid resuscitation and may require the use of vasosuppressors.

A patient presenting a SIRS is generally admitted to intensive care when the condition involves continuously monitoring vital signs and, if appropriate, the use of substitution methods (transfusion of blood derivatives, vascular fluid resuscitation, mechanical ventilation, catecholamines, isodialysis, extracorporal circulation, etc.). The ultimate aim of intensive care is to restore homeostasis.

The term "complications" means an infection other than that which has caused the systemic inflammatory response syndrome, said infection then being termed a secondary infection, or indeed a primary infection when the systemic inflammatory response syndrome is caused by an insult other than an infection. The term "complications" can also mean the death of the patient. Said primary or secondary infection may or may not be nosocomial. Nosocomial infections are contracted exclusively in the case of hospitalization and they appear at least 48 hours (h) after said hospitalization.

The term "risk of complications" means the risk to a patient of generating a primary or secondary infection, or the risk that the patient might die. The presence of a risk of complications corresponds to the risk that the complication will arise, for example within 60 days, in particular within 40 days, especially within 30 days following admission of a patient sustaining a SIRS to intensive care, or the onset of septic shock in the case of a patient in a state of septic shock or who has previously been in a state of septic shock, and especially or moreover corresponds to the risk that the complications will arise during the entire duration of the stay in intensive care, or even of hospitalization.

The method of the invention may thus be a method of evaluating the risk to a patient of generating an infection (which will be primary for a patient who has sustained an insult, and not an infection that has generated the systemic inflammatory response syndrome, and which will be secondary for a patient who has suffered a first infection that is the source of the systemic inflammatory response syndrome). Under such circumstances, the method of the invention may be used to provide a conclusion as to the presence or otherwise of a risk to the patient of generating such an infection.

The method of the invention is a method carried out in vitro or ex vivo. It has the advantage of being capable of readily evaluating the risk of complications, and in particular of mortality, in particular of a patient who is admitted to an intensive care unit, by providing a marker that is measurable directly, in contrast to SOFA and SAPSII severity scores, for example, and in which the measurement can be carried out in a nearby laboratory or at the patient's bedside. Measuring the quantity of one or more transcripts of the IL7R gene is entirely suited to being carried out by using automated analysis instruments or by using rapid tests.

Preferably, said patient is in a septic state, especially in severe sepsis, or in septic shock. This state corresponds to the state of the patient at the time the test sample is taken or to the state of the patient as it was very recently before the test sample was taken, in particular as it was within the 6 days preceding taking the test sample. With sepsis, severe sepsis, or septic shock in particular, it is possible for the patient to be in this state, in particular on admission to the intensive care unit, and it is possible for the sepsis, severe sepsis, or septic shock to have ceased by the time the test sample is taken. In the remainder of the description, under such circumstances, the patient is said to have sustained or to be in a state of septic shock, sepsis, or severe sepsis, as the case may be. In particular, in the method of the invention, the biological test sample is obtained from a patient presenting with sepsis, in particular a severe sepsis or from a patient who has previously presented a sepsis, in particular a severe sepsis within the 6 days preceding taking the biological test sample, or indeed the biological test sample is obtained from a patient in a state of septic shock or who has previously been in a state of septic shock within the 6 days preceding taking the biological test sample.

The method of the invention is also entirely suitable for patients with a SIRS, due to an insult other than an infection, especially surgery, a burn, or trauma.

Preferably, the risk of complications evaluated in the context of the invention is the risk of death of the patient. The method of the invention may therefore be a method of evaluating the likelihood that the patient will die. Under such circumstances, the method of the invention may be used to provide a conclusion as to the presence or otherwise of a risk that the patient will die. When predicting the risk of death, this risk is evaluated for death occurring within 60 days, in particular within 40 days, especially within 30 days, in particular within 28 days, following admission of the patient to the intensive care unit, and especially for death that might occur throughout the entire stay in intensive care, or indeed of hospitalization. As stated above, the present invention presents a preferred application in patients who present a sepsis, in particular severe sepsis, or indeed in patients in septic shock or who have previously suffered a septic shock. Preferably, the method of the present invention is used to evaluate the risk of mortality in such patients. Particularly preferably, the method of the present invention is more particularly advantageous in evaluating the risk of mortality in a patient who is or who has previously been in a state of septic shock. Under such circumstances, the risk of death is evaluated for death occurring within 60 days, in particular within 40 days, especially within 30 days, in particular within 28 days following the onset of the septic shock, and especially for death that might occur throughout the entire stay in intensive care, or indeed of hospitalization.

Preferably within the context of the invention, said at least one transcript of the IL7R gene that is detected and preferably quantified is selected from the transcripts IL7R-001 of SEQ ID NO: 2, IL7R-002 of SEQ ID NO: 3, IL7R-003 of SEQ ID NO: 4, IL7R-005 of SEQ ID NO: 6, and IL7R-007 of SEQ ID NO: 8 and their variants, the sequence of a variant having at least 99% identity with one of said sequences. The percentage identity is determined using sequence alignment software such as CLUSTALW (Nucleic Acids Res. 1994 Nov. 11; 22(22):4673-80. CLUSTAL W: Improving the sensitivity of progressive multiple sequence alignment through sequence weighting, position-specific gap penalties and weight matrix choice). In particular, a variant corresponds to a polymorphism of the sequence of the IL7R gene. In particular, said at least one transcript of the IL7R gene is selected from transcripts comprising at least a portion of the transmembrane domain, or indeed the entire transmembrane domain, of CD127, and preferably corresponds to the transcript IL7R-001 of SEQ ID NO: 2 or to one of its variants having at least 99% identity with said sequence. The transcript IL7R-001 of SEQ ID NO: 2 has the advantage of being detected in large quantities compared with other transcripts, which facilitates implementation of the method of the invention, when detecting at least this transcript.

The term "transcript", means the RNA, and in particular the messenger RNA obtained from transcription of the IL7R gene. More precisely, the transcripts are the RNAs produced by splicing the gene. In the context of the invention, the transcript or the transcripts of the IL7R gene detected and/or quantified is(are) thus preferably a mRNA.

In particular, a method of the invention employs the steps consisting in:
 i) determining the quantity of said at least one transcript of the IL7R gene in said biological sample from a patient, termed the test sample;
 ii) comparing the quantity of said at least one transcript determined for said biological sample or a value derived from this quantity with a predetermined reference value; and iii) from the result of the comparison, coming to a conclusion as to the possible presence of a risk of complications.

It is possible, within the context of the invention, to detect and quantify several transcripts of the IL7R gene, and in particular to detect and quantify the transcripts IL7R-001 of SEQ ID NO: 2, IL7R-002 of SEQ ID NO: 3, IL7R-003 of SEQ ID NO: 4, IL7R-005 of SEQ ID NO: 6, and IL7R-007 of SEQ ID NO: 8.

If, within the context of the invention, a plurality of transcripts of the gene IL7R are detected, the method implements in particular the steps consisting in:
  i) determining the overall quantity of a plurality of transcripts of the IL7R gene in said biological sample from a patient;
  ii) comparing the overall quantity of said transcripts determined for said biological sample or a value derived from this quantity with a predetermined reference value; and
  iii) from the result of the comparison, coming to a conclusion as to the possible presence of a risk of complications.

In the context of the invention, at least one transcript of the IL7R gene is detected in a biological sample obtained from a patient for whom a risk of complications is to be evaluated, termed the test sample. The result obtained from this detection is compared with a reference value in order to evaluate the risk of complications.

Thus, under all circumstances, in addition to measuring the quantity of said at least one transcript of a IL7R gene per se in the test sample, the method of the invention may comprise previously obtaining a reference value for comparing with the quantity of said at least one determined transcript detected in the test sample or a value derived from this quantity, in order to conclude whether there exists a risk of complications in the patient from whom the test sample was obtained. It is also possible for this reference value to be available in the future when carrying out the method of the invention.

The reference value can be determined from the same transcript or transcripts of the IL7R gene as that or those detected or quantified in the biological test sample. However, it could be determined on a biological sample that is different but of the same type, whether obtained from the same patient or from another patient or from a pool of patients. When one or more samples obtained from a reference patient or pool of reference patients is (are) to be used to determine the reference value, the samples should preferably be of the same type of SIRS (in particular sepsis, severe sepsis, or septic shock) as the patient for whom the method is to be carried out.

The test sample in the context of the method of the invention is a biological sample originating from the patient for whom the risk of complications is to be evaluated. In particular, such a biological sample is selected from those that are suspected of containing transcripts of the IL7R gene. As an example, the test sample originates from a sample obtained within the 6 days or on day 6 (D6) following admission of a patient with a SIRS to the intensive care unit, preferably within the 5 days or on day 5 (D5) following admission to the intensive care unit, more preferably within the 4 days or on day 4 (D4) following admission to the intensive care unit, yet more preferably within the 3 days or on day 3 (D3) following admission to the intensive care unit, or indeed within the 2 days or on day 2 (D2) following admission to the intensive care unit, or indeed within the 24 h or 24 h (D1) following admission to the intensive care unit.

When the SIRS corresponds to a septic shock, these timescales should indeed be calculated from the onset of septic shock, which may be defined by the onset of the administration of catecholamines to the patient. In addition, with patients in a state of septic shock or who have presented a septic shock, the test sample preferably originates from a sample obtained within the 6 days or on day 6 (D6) following the onset of septic shock, preferably within the 5 days or on day 5 (D5) following the onset of septic shock, more preferably within the 4 days or on day 4 (D4) following the onset of septic shock, yet more preferably within the 3 days or on day 3 (D3) following the onset of septic shock, or indeed within two days or on day 2 (D2) following the onset of septic shock, or indeed within the 24 h or 24 h (D1) following the onset of septic shock. In other words, the test sample is preferably obtained from a sample taken from the patient for whom a risk of complications is to be evaluated, within the 6 days, within the 5 days, within the 4 days, within the 3 days, within the 2 days, or within 24 h, especially on day 6, on day 5, on day 4, on day 3, on day 2 or at 24 h following admission to the intensive care unit or the onset of septic shock, respectively.

When the method of the invention is not applied to a patient admitted into the intensive care unit, but to a patient who has undergone surgery, especially major surgery (of the cardiac or abdominal type, for example) or transplantation, where monitoring takes place in a unit other than the intensive care unit, the times indicated in the context of the description of the invention for taking the samples concerned should not be calculated from admission to the intensive care unit, but from the start of surgery.

In the context of the invention, it is also possible for the comparison carried out in step iii) to use a ratio between the quantity of transcript(s) determined for a biological sample from said patient corresponding to a sample taken at a time t (in particular within the 3 days or on day 3 (D3)) and the quantity of transcript(s) determined for a biological sample from said patient corresponding to a sample taken at a time t' (in particular within 24 hours or at 24 hours (D1)).

The samples on which the method of the invention is carried out, also termed the test samples, are of human origin.

The test sample may be a biological fluid, for example selected from blood, whole blood, in particular such as that collected from a vein, i.e. containing white and red cells, platelets, and plasma, or indeed a sample of serum or of plasma, as well as components of said fluids, such as PBMC (Peripheral Blood Mononuclear Cells), or excreted vesicles such as cells or apoptotic bodies, or excreted vesicles, in particular those comprising exosomes and microvesicles. Preferred biological samples, whether they be biological test samples or samples used to determine the reference value, are preferably samples of whole blood or PBMC.

The samples from which the reference values may be determined, also termed "reference samples", may be of various natures, and in particular they may be biological in nature, as mentioned above for the test sample (biological fluids), or they may be otherwise, in particular they may be synthesized samples containing a calibrated quantity of selected transcript(s). Advantageously, if these reference samples are biological samples, they should be of the same nature as the biological test sample, or at the very least they should be of a compatible nature in order to constitute a reference as regards detecting and/or quantifying the transcript or transcripts of the selected IL7R gene. In particular, when the method is carried out on human subjects, a reference biological sample should be a human biological sample. Also preferably, biological samples corresponding to the same biological fluid or to the same component(s), for example samples of whole blood, should be used both for the test sample and for the reference sample.

Any method of detecting and/or quantifying transcript that is well known to the person skilled in the art may be used to carry out the invention. In particular, such methods may use one or more binding partners for the selected transcript(s).

In general, it is known that the results of analyte detection tests depend to a large extent on the characteristics of the binding partners used. Thus, when detecting RNA by hybridization with nucleotide probes, the results depend in particular on the characteristics of size, composition, and percentage complementarity of the probes, and these characteristics influence the values measured with these probes. Thus, it can be understood that it is not possible to provide precise reference values and that the reference value or values adapted to each binding partner used may be determined in each case by simple, routine experiments.

In particular, the reference value should be selected as a function of the method used to determine the quantity of said at least one transcript of the IL7R gene and should be representative of the population from which the patient for whom the risk is to be evaluated originates.

As a function of the comparison to be carried out, the person skilled in the art is able to determine the reference value for comparing with the quantity of said at least one transcript determined for said biological sample or with the value derived from this quantity used for the comparison. In particular, a suitable statistical test could be used in order to determine this reference value. As an example, it is possible to make a comparison between different populations or types of samples, on the basis of changes over time in a single population or a single type of sample. It should be understood that the term "reference value" is used herein to denote either a discrete value or a range of values corresponding to a range of uncertainty. Clearly, when the measured value is included in the range of uncertainty, or is very close to the reference value when a discrete value is used, it is not possible to come to a definitive conclusion, and additional investigations should be carried out.

In the context of the invention, the reference value may be determined in various ways: in particular, either the reference value is obtained from a reference sample obtained from the same patient and obtained when an earlier sample was taken, or the reference value is obtained from a reference sample from a reference individual or from reference samples from a reference population.

A reference value obtained from a reference sample obtained from the same patient obtained when an earlier sample was taken is termed an "internal" reference. A reference value obtained from a reference sample from a reference individual or reference samples from a reference population is termed an "external" reference value.

An internal reference value may correspond to or be derived from the quantity of said at least one transcript of the IL7R gene measured in a biological sample obtained from the same said patient when an earlier sample was taken, i.e. in a biological sample obtained from the patient for whom the risk of complications is to be evaluated and obtained previously to the test sample. The term "previously" or "earlier" means before that time.

Preferably, an internal reference value is obtained from a biological sample that directly precedes the test sample, i.e. that precedes the test sample in the order of samples taken from the patient.

In accordance with a particularly advantageous implementation, the internal reference sample is obtained from a sample obtained within the 2 days or within one day, or indeed on day 2 or on day 1 after admitting the patient to intensive care, which means that the risk of complications in the patient tested can be determined very early on. When the patient is in a state of septic shock or has previously been in a state of septic shock, these time intervals should be calculated from the onset of septic shock.

By way of example, the earlier sample may be taken within 48 h or 48 h following the patient's admission to intensive care, and preferably at least 24 h before taking the test sample. Preferably, the earlier sample is taken 24 h after admission to intensive care, and the sample corresponding to the test sample is taken 72 h after admission to intensive care. For a patient in a state of septic shock or who has previously been in a state of septic shock, the earlier sample is preferably taken within 48 h or 48 h following the onset of septic shock and preferably at least 24 h before taking the test sample. Preferably, the earlier sample is taken 24 h after the onset of septic shock and the sample corresponding to the test sample is taken 72 h after the onset of septic shock.

Preferably, the method of the invention can be used to conclude whether there is a risk of complications, and in particular of mortality in the patient, when the quantity of said at least one transcript determined for said biological test sample or a value derived from this quantity that is measured in the test sample does not increase significantly compared with the internal reference value. It is within the purview of the person skilled in the art to determine what percentage increase is significant, which will depend in particular on the type of the test sample (for example whole blood, PBMC, cell sub-populations), on the type of analysis, or indeed on the instrument on which the analysis is carried out, as a function of whether it is specificity that is to be favored in an exclusion test or sensitivity that is to be favored in an inclusion test, depending on the treatment to be applied or indeed on the disease from which the patient is suffering.

Specifically, when using an external reference value, this may correspond to or be obtained from the quantity of said at least one transcript, measured in a biological sample obtained from a patient who has sustained an insult or an infection generating a systemic inflammatory response syndrome and who is known not to have suffered any complications, in particular a patient presenting a sepsis who is known not to have suffered any complications, and preferably a patient in septic shock who is known not to have suffered any complications.

In particular, when the risk of complications to be evaluated is a risk of mortality, the external reference value may correspond to or be obtained from the quantity of said at least one transcript, measured in a reference biological sample obtained from a patient who has sustained an insult or an infection generating a systemic inflammatory response syndrome and who is known to have survived, in particular a patient presenting a sepsis who is known to have survived, and preferably a patient in septic shock who is known to have survived.

Under such circumstances, the determined quantity of said at least one transcript that serves to determine the external reference value is preferably measured in parallel, i.e. at the same time, as measuring the quantity of said at least one transcript of the IL7R gene in the sample obtained from the patient for whom the risk of complications is to be evaluated, even though the reference biological sample was taken before taking the test sample.

The reference value may also correspond to or be obtained from a mean value for the quantity of said at least one transcript that is measured on a pool of samples obtained from patients who have sustained an insult or an infection generating a systemic inflammatory response syndrome (SIRS), and who are known not to have suffered any complications, in particular patients presenting a sepsis who are known not to have suffered any complications, and preferably patients in a state of septic shock who are known not to have suffered any complications.

In particular, when the risk of complications to be evaluated is a risk of mortality, the reference value may also correspond to or be obtained from a mean value for the quantity of said at least one transcript that is measured for a pool of samples obtained from patients who have sustained an insult or an infection generating a systemic inflammatory response syndrome (SIRS), and who are known to have survived, in particular patients presenting a sepsis who are known to have survived, and preferably patients in a state of septic shock who are known to have survived.

Under such circumstances, the external reference value is preferably determined before the quantity of said at least one transcript of the IL7R gene is measured in the sample obtained from the patient whose risk of mortality is to be evaluated, the reference samples, which are intended to be pooled, being taken before taking the test sample.

In particular, an increased risk of complications, and in particular of mortality, in said patient is concluded when the quantity of said at least one transcript of the IL7R gene in the biological sample from the patient is significantly reduced compared with the value for the external reference. This applies in particular when the prognosis is based on taking into consideration the quantity of the transcript IL7R-001, IL7R-002, IL7R-003, IL7R-005, or IL7R-007, or the overall quantity of a plurality of transcripts, preferably comprising 2, 3, 4, or all of the transcripts selected from the transcripts IL7R-001, IL7R-002, IL7R-003, IL7R-005, and IL7R-007.

The person skilled in the art is able to determine when a reduction is judged to be significant, in particular as a function of the type of samples being tested (for example whole blood or PBMC), of the type of detection being carried out (with or without amplification), or indeed the analysis instrument used, depending on whether it favors specificity for an exclusion test, or sensitivity for an inclusion test, depending on the treatment to be applied, or indeed on the disease from which the patient is suffering.

In particular, the biological test sample is obtained from a patient who is in a state of septic shock at the time when the biological test sample is taken, or who has previously been in a state of septic shock, and the reference value is said to be external and corresponds to or is derived from the quantity of said at least one transcript of the IL7R gene measured in a biological reference sample obtained from a patient who is in a state of septic shock at the time when the reference sample is taken or who has previously been in a state of septic shock, and who is known not to have suffered any complications, and in particular who is known to have survived, or indeed corresponds to a mean value for the quantity of said at least one transcript of the IL7R gene that is measured for a pool of reference samples obtained from patients in a state of septic shock at the time the reference samples are taken or who have been in a state of septic shock, who are known not to have suffered any complications, and in particular who are known to have survived.

In order to obtain such an external reference value, the reference sample or samples used are preferably obtained from those having the same characteristics or a majority of common characteristics, in particular the same sex and/or similar or identical ages and/or of the same ethnic origin, with those of the subject or patient for whom the risk of complications, and in particular of mortality, is to be evaluated. Under such circumstances, the reference sample may also be constituted by any biological or non-biological sample that has previously been calibrated in order to contain the quantity of said at least one transcript of the IL7R gene that corresponds to the mean quantity measured in a pool of samples from patients who have sustained an insult or an infection generating a systemic inflammatory response syndrome (and in particular patients presenting a sepsis, and preferably patients in a state of septic shock), and who are known not to have suffered any complications, and preferably who are known to have survived, or that has already been calibrated in order to contain the quantity of said at least one transcript of the IL7R gene that corresponds to the mean quantity measured in a pool of samples from patients who have sustained an insult or an infection generating a systemic inflammatory response syndrome (and in particular patients presenting a sepsis, and preferably patients in a state of septic shock), and who are known not to have suffered any complications, and preferably who are known to have survived.

Similarly, for determining the external reference value, and for detecting or quantifying said at least one transcript of the IL7R gene in the test sample, it is preferable to use samples that are taken at the same time, in particular in respect of admission to the intensive care unit or in respect of the onset of septic shock, as the case may be.

In particular, the biological test sample should be obtained from a patient who is in a state of septic shock at the time the biological test sample is taken or who has previously been in a state of septic shock, and the quantity of said at least one transcript of the IL7R gene should be measured in a test sample and, if appropriate, in the biological sample or samples used to obtain the external reference value, which correspond(s) to a sample taken within the 6 days following the onset of septic shock, preferably the 3rd day following the onset of septic shock, and in particular 72 h after the onset of septic shock.

More generally, when the biological test sample is obtained from a patient who has sustained an insult or an infection generating a systemic inflammatory response syndrome who has been admitted to the intensive care unit, the quantity of said at least one transcript of the IL7R gene is measured in a test sample and, if appropriate, in the biological sample or samples used to obtain the external reference value, obtained from a sample that is preferably taken within the 6 days following the patient's admission to intensive care, preferably the 3rd day following admission, and in particular 72 h following admission.

In particular, for a patient in a state of septic shock at the time the biological test sample is taken or who has previously been in a state of septic shock, in step ii) of the methods of the invention, the comparison could be carried out directly from the measured quantity of said at least one transcript of the IL7R gene, both for the test sample and for determining the external reference value, in a biological sample taken on the $3^{rd}$ day following the onset of septic shock, and in particular 72 h thereafter, or from the ratio between the measured quantity of said at least one transcript of the IL7R gene, both for the test sample and for determining the external reference value, in a biological sample taken on the $3^{rd}$ day following the onset of septic shock, and in particular 72 h thereafter, and the quantity, both for the test sample and for determining the reference value, in a biological sample obtained within 24 h and in particular 24 h following septic shock. Under such circumstances, the comparison is carried out in step iii) between:

the ratio of the quantity of transcript(s) determined for a biological sample from a patient for whom the diagnosis is to be obtained, corresponding to a sample taken at a time t (especially within the 3 days or on day 3 (D3) following the onset of septic shock) to the quantity of transcript(s) determined for a biological sample from said patient, corresponding to a sample taken at a time t' (especially within 24 hours or 24 hours (D1) following the onset of septic shock); and the ratio of the quantity of transcript(s) determined for a biological sample from a patient or from the reference population, corresponding to a sample taken at a time t (especially within the 3 days or on day 3 (D3) following the onset of septic shock) to the quantity of transcript(s) determined for a biological sample from said patient or reference population, corresponding to a sample taken at a time t' (especially within 24 hours or 24 hours (D1) following the onset of septic shock).

More generally, when the biological test sample is obtained from a patient who has sustained an insult or an infection generating a systemic inflammatory response syndrome and who has been admitted to the intensive care unit, the comparison is, preferably, carried out directly from the measured quantity of said at least one transcript of the gene IL7R, for the test sample, and for determining the external reference value, in a biological sample taken on the 3rd day following admission of the patient to the intensive care unit (and in particular 72 h thereafter) or from the ratio between the measured quantity of said at least one transcript of the gene IL7R, for the test sample, and for determining the external reference value, in a biological sample taken on the 3rd day following the admission (and in particular 72 h thereafter) and the quantity measured, for the test sample and for determining the reference value, in a biological sample taken within 24 h, and especially 24 h following the septic shock.

Under such circumstances, the comparison is carried out in step iii) between:

the ratio of the quantity of transcript(s) determined for a biological sample from a patient for whom the diagnosis is to be obtained, corresponding to a sample taken at a time t (especially within the 3 days or on day 3 (D3) following admission to intensive care) to the quantity of transcript(s) determined for a biological sample from said patient, corresponding to a sample taken at a time t' (especially within 24 h or 24 h (D1) following admission to intensive care); and the ratio of the quantity of transcript(s) determined for a biological sample from a patient or from the reference population corresponding to a sample taken at a time t (especially within the 3 days or on day 3 (D3) following the onset of septic shock) to the quantity of transcript(s) determined for a biological sample from said patient or reference population corresponding to a sample taken at a time t' (especially within 24 h or 24 h (D1) following the onset of septic shock).

In the context of the invention, the term "detecting a transcript" means detecting said transcript per se in the biological sample, by direct detection of said transcript, using any method known to the person skilled in the art for determining the presence of said transcript in a sample, or by indirect detection of the transcript after transformation thereof into DNA, or after amplification of said transcript or after amplification of the DNA obtained after transformation of said transcript into DNA. In the context of the invention, detection is accompanied by quantifying the selected transcript or transcripts, i.e. the concentration of a transcript or of a plurality of transcripts, in the general or individual case, is determined directly or indirectly.

A transcript in a biological sample may be detected directly by using any means known to the person skilled in the art such as, for example, by hybridization with a bonding partner that may or may not be specific for the transcript to be detected, if appropriate after amplification using a PCR technique, with or without a probe, or NASBA or, for example, by sequencing (Cloonan et al., 2008; Emrich et al., 2007; Mortazavi et al., 2008).

The term "hybridization" means the process during which, under appropriate conditions, two nucleotide fragments bond together with stable and specific hydrogen bonds in order to form a double-stranded complex.

The "bonding partners" of a transcript to be detected are any partner that could bond to said transcript, and in particular specific bonding partners. Examples of specific bonding partners that may be cited are hybridization probes and amplification primers, and any other molecule that is capable of binding to the transcript to be detected. It is possible to use specific bonding partners, i.e. binding essentially or even exclusively to a single transcript or binding to a plurality of transcripts of the IL7R gene, as is illustrated in the examples below.

The term "hybridization probe" means a nucleotide fragment comprising 5 to 100 nucleic motifs, in particular 10 to 35 nucleic motifs, having a hybridization specificity under predetermined conditions in order to form a hybridization complex with one or more transcripts of the IL7R gene. The hybridization probe may comprise a marker allowing it to be detected, and is then termed a "detection probe".

Within the meaning of the present invention, the term "amplification primer" means a nucleotide fragment comprising 5 to 100 nucleic motifs, preferably 15 to 30 nucleic motifs, allowing initiation of an enzymatic polymerization, in particular such as an enzymatic amplification reaction. The term "enzymatic amplification reaction" means a process generating multiple copies of a nucleotide fragment by the action of at least one enzyme. Such amplification reactions are well known to the person skilled in the art and the following techniques may be cited in particular:

PCR (Polymerase Chain Reaction), as described in U.S. Pat. Nos. 4,683,195, 4,683,202 and 4,800,159;

LCR (Ligase Chain Reaction), disclosed, for example, in patent application EP 0 201 184;

RCR (Repair Chain Reaction), described in patent application WO 90/01069;

3SR (Self-Sustained Sequence Replication) in patent application WO 90/06995;

NASBA (Nucleic Acid Sequence-Based Amplification) in patent application WO 91/02818;

TMA (Transcription Mediated Amplification) in U.S. Pat. No. 5,399,491; and

LAMP (Loop-mediated Isothermal Amplification) in U.S. Pat. No. 6,410,278.

When the enzymatic amplification is a PCR, it is carried out after a reverse transcript reaction carried out in one or two steps and is conventionally known as RT-PCR (RT for "reverse transcription"). During RT-PCR, the specific reagent for one or more transcripts comprises at least two amplification primers that are either specific for the target transcript or transcripts in the case of one-step RT-PCR (EP 0 569 272), or specific for the DNA or DNAs corresponding to the target transcript(s) in the case of two-step RT-PCR (Goblet et al., 1989).

The term "detection" means either a physical method or a chemical method with an intercalating dye such as SYBR® Green I or ethidium bromide, or a detection method using a marker. Many detection methods exist for the detection of nucleic acids (Keller G. H., 1993; Kricka, 1999).

The term "marker" means a tracer that is capable of producing a signal that can be detected. A non-limiting list of these tracers includes enzymes that produce a detectable signal, for example by colorimetry, fluorescence, or luminescence, such as horseradish peroxidase, alkaline phosphatase, beta-galactosidase, glucose-6-phosphate dehydrogenase; chromophores such as fluorescent, luminescent, or dye compounds; electron-dense groups detectable by electron microscopy or by their electrical properties such as conductivity, by amperometric, or voltametric methods, or by impedance measurements; groups that are detectable by optical methods such as diffraction, surface plasmon resonance, contact angle variation, or by physical methods such as atomic force spectroscopy, the tunnel effect, etc.; radioactive molecules such as $^{32}P$, $^{35}S$ or $^{125}I$.

In the context of the present invention, the hybridization probe may be a probe termed a detection probe. Under such circumstances, the "detection" probe is tagged with a marker as defined above. Because of the presence of this marker, the presence of a hybridization reaction between a given detection probe and the transcript to be detected can be detected.

Regarding real time quantitative PCR, for diagnostic applications, two types of tagging for a specific hybridization are generally used:

Firstly, it is possible to use methods employing a probe between two primers. In particular, it is possible to use TaqMan®, probes, such as those described by Espy et al., 2006; Heid et al., 1996; Holland et al., 1991; molecular tags, also known as molecular beacons, such as those described by Espy et al., 2006; Mhlanga and Malmberg, 2001; Sigma, 2008; adjacent hybridization probes, known as HybProbes (FRET); or indeed CPT (for "cycling probe technology"), as described by Duck et al., 1990.

It is also possible to use methods employing tagged primers. Primers of this type may be scorpion primers or Scorpion®, as described by Sigma, 2008; Plexor primers, as described by Buh Gasparic et al., 2010; primers used in the AmpliFluor® technique, as described by Bio-Rad Laboratories, 2006; Nazarenko et al., 1997; LUX (light upon extension) primers, as described by Bio-Rad Laboratories, 2006; Buh Gasparic et al., 2010; Nazarenko et al., 2002; or indeed BD Qzyme™ primers, as described by Bio-Rad Laboratories, 2006; Clontech, 2003.

The hybridization probe may also be a probe termed a capture probe. Under such circumstances, the probe termed a capture probe is immobilized or can be immobilized on a solid support using any appropriate means, i.e. directly or indirectly, for example by covalence or adsorption. The solid support that may be used may be synthesized materials or natural materials, optionally chemically modified, in particular polysaccharides such as materials based on cellulose, for example paper, cellulose derivatives such as cellulose acetate and nitrocellulose or dextran, polymers, copolymers, in particular based on styrene type monomers, natural fibers such as cotton, and synthetic fibers such as nylon; mineral materials such as silica, quartz, glass, or ceramics; latexes; magnetic particles; metallic derivatives; gels, etc. The solid support may be in the form of a microtitration plate, or a membrane as described in the application WO-A-94/12670, or a particle.

It is also possible to immobilize a plurality of different capture probes on the support, each probe being specific for a target transcript. In particular, it is possible to use as the support a biochip on which a large number of probes may be immobilized. The term "biochip" means a solid support of small dimensions on which a multitude of capture probes are fixed at predetermined positions. The concept of a biochip or DNA chip dates from the beginning of the 1990s. It is based on a multidisciplinary technology that combines microelectronics, nucleic acid chemistry, image analysis, and data processing. The operating principle is based on a cornerstone of molecular biology: the hybridization phenomenon, i.e. pairing by the complementarity of bases of two DNA and/or RNA sequences. The biochip method is based on the use of capture probes fixed to a solid support on which a sample of target nucleotide fragments tagged directly or indirectly with fluorochromes is caused to act. The capture probes are positioned in a specific manner on the support or chip and each hybridization produces a particular piece of information pertaining to the target nucleotide fragment. The information obtained is cumulative and can, for example, be used to quantify the target transcript or plurality of target transcripts. After hybridization, the support or chip is washed and the transcript/capture probe complexes are revealed by a high affinity ligand bonded, for example, to a fluorochrome type marker. The fluorescence is read, for example, by a scanner and the fluorescence is processed digitally. By way of indication, DNA chips developed by Affymetrix ("Accessing Genetic Information with High-Density DNA arrays") (Chee et al., 1996; Pease et al., 1994), may be cited for the molecular diagnostics. In this technology, the capture probes are generally small, about 25 nucleotides. Other examples of biochips are given in many publications (Cheng et al., 1998, 1996; Ginot, 1997; Livache et al., 1994; Ramsay, 1998) or in the U.S. Pat. Nos. 4,981,783, 5,700,637, 5,445,934, 5,744,305, and 5,807,522. The principal characteristic of the solid support must be to preserve the hybridization characteristics of the capture probes on the target nucleotide fragments while generating minimal background noise for the detection method.

The techniques for immobilizing probes on a support are well known to the person skilled in the art; examples are depositing pre-synthesized probes by printing or microdeposition (patent applications WO-A-00/71750, FR 00/14896, FR 00/14691), or indeed in situ synthesis (patent applications WO 89/10977 and WO 90/03382).

In order to detect the transcript of the biological sample, an extraction step might be necessary. The extraction is carried out using any of the protocols for extracting and purifying nucleic acids that are well known to the person skilled in the art. By way of indication, nucleic acids could be extracted by means of:

a step for lysis of cells present in the biological sample in order to liberate the nucleic acids contained in the patient's cells. By way of example, lysis methods such as those described in the following patent applications could be used:
WO 00/05338, regarding mixed magnetic and mechanical lysis;
WO 99/53304, regarding electrical lysis;
WO 99/15321, regarding mechanical lysis.

The person skilled in the art could use other well-known lysis methods, such as thermal shock or osmotic shock, or chemical lysis using chaotropic agents such as guanidinium salts (U.S. Pat. No. 5,234,809).

a step for purification, in order to separate the nucleic acids from the other cellular constituents precipitated out in the lysis step. This step may be used in general to concentrate the nucleic acids, and could be adapted to the purification of RNA. By way of example, magnetic particles, optionally coated with oligonucleotides, by adsorption or covalence, could be used (see the patents U.S. Pat. Nos. 4,672,040 and 5,750,338 in this regard), then the nucleic acids that are fixed to these magnetic particles are purified by means of a washing step. This step for purifying the nucleic acids is of particular interest if said nucleic acids are to be amplified subsequently. One particularly advantageous implementation of these magnetic particles is described in patent applications WO-A-97/45202 and WO-A-99/35500. It is also possible to use silica, either in the form of a column, or in the form of inert particles (Boom et al., 1990) or magnetic particles (Merck: MagPrep® Silica, Promega: MagneSil® paramagnetic particles). Other very popular methods are based on ion exchange resins in a column or in a particulate paramagnetic form (Whatman: DEAE-Magarose) (Levison et al., 1998). Another method is that of adsorption onto a metallic oxide support (Xtrana: Xtra-Bind® matrix).

When the RNA is to be extracted specifically from a biological sample, extraction may in particular be carried out using phenol, chloroform, and alcohol in order to eliminate the proteins and precipitate the RNA with 100% ethanol. The RNA can then be pelletized by centrifuging, washing, and being taken up again into solution.

Detection and quantification methods of this type may be used to determine the quantity of one or more transcripts present in the test sample or to provide a derived value. By way of example, a derived value of the quantity may be the absolute concentration, calculated using a calibration curve obtained from successive dilutions of a solution of amplicon with a known concentration. It may also correspond to the value of the normalized and calibrated quantity, such as the CNRQ (Calibrated Normalized Relative Quantity, (Hellemans et al., 2007)), which integrates the values for a reference sample, a calibrator, and one or more reference genes. Examples of reference genes that may be cited are the genes PPIB, PPIA, GLYR1, RANBP3, HPRT1, 18S, GAPDH, RPLPO and ACTB.

The quantities of a plurality of transcripts may be determined sequentially or simultaneously, using methods that are routine to the person skilled in the art, as indicated above.

In the context of the invention, the quantity of said at least one transcript of the IL7R gene is preferably measured by quantitative RT-PCR.

In particular, the quantity of said at least one transcript of the IL7R gene is measured with at least one of the following amplification primer pairs, with or without the probe mentioned:

forward primer with SEQ ID NO: 12 and reverse primer with SEQ ID NO: 13, and optionally probe with SEQ ID NO: 14, which can be used to detect the transcripts IL7R-001, IL7R-002, IL7R-003, IL7R-005, and IL7R-007 and their variants;

forward primer with SEQ ID NO: 15 and reverse primer with SEQ ID NO: 16, and optionally probe with SEQ ID NO: 17, which can be used to detect the transcript IL7R-001 and its variants;

forward primer with SEQ ID NO: 18 and reverse primer with SEQ ID NO: 19, and optionally probe with SEQ ID NO: 20, which can be used to detect the transcript IL7R-001 and its variants.

All of the indications and preferences mentioned above pertaining to detecting and quantifying the transcript or transcripts of the IL7R gene selected apply equally to detecting or quantifying in the test sample or in the reference sample.

In order to carry out the method of the invention, the invention also pertains to a diagnostic kit comprising the tools and/or reagents necessary for detecting at least one transcript of the IL7R gene.

By way of non-limiting example of the reagents necessary for detecting one or more transcripts of the IL7R gene, mention may be made of the bonding partners of said transcript or transcripts, such as hybridization probes or amplification primers.

In particular, the invention concerns kits for the in vitro or ex vivo measurement of the quantity of at least one transcript of the IL7R gene in a biological sample, comprising:

specific reagents or tools for measuring the quantity of said at least one transcript of the IL7R gene in said biological sample; and a control sample that is a sample that is calibrated in order to contain the quantity of said at least one transcript of the IL7R gene that corresponds to the mean quantity measured in a pool of samples from patients who have sustained an insult or an infection generating a systemic inflammatory response syndrome, who are known not to have suffered any complications, and preferably who are known to have survived, and/or a control sample that is a sample that is calibrated in order to contain the quantity of said at least one transcript of the IL7R gene that corresponds to the mean quantity measured in a pool of samples from patients who have sustained an insult or an infection generating a systemic inflammatory response syndrome, who are known to have suffered complications, and preferably who are known not to have survived.

In particular, such a kit contains, as specific reagents for measuring the quantity of said at least one transcript of the IL7R gene in said biological sample, at least one of the following pairs of amplification primers, with or without the probe mentioned:

forward primer with SEQ ID NO: 12 and reverse primer with SEQ ID NO: 13, and optionally probe with SEQ ID NO: 14;

forward primer with SEQ ID NO: 15 and reverse primer with SEQ ID NO: 16, and optionally probe with SEQ ID NO: 17;

forward primer with SEQ ID NO: 18 and reverse primer with SEQ ID NO: 19, and optionally probe with SEQ ID NO: 20.

A control sample may be a sample containing a given concentration of target transcript(s) or of corresponding complementary DNA, which may be either a synthesized sample containing a calibrated concentration of target transcript(s) or of corresponding complementary DNA, or a biological sample. A control sample may in particular be a biological sample obtained from at least one patient who has sustained an insult or an infection generating a systemic inflammatory response syndrome, who is known not to have suffered any complications, and especially who is known to have survived, or indeed a biological sample obtained from at least one patient who has sustained an insult or an infection generating a systemic inflammatory response syndrome who is known to have suffered complications, and especially who is known not to have survived. This type of control sample is in particular obtained from one or more patient(s) who has/have sustained an insult such as surgery, burns, trauma, etc., or an infection generating a systemic inflammatory response syndrome (SIRS), especially one or more patient(s) presenting a sepsis, and preferably one or more patient(s) in a state of septic shock.

The invention also encompasses the use of a kit of the invention for carrying out the method of the invention, and in particular for evaluating the risk of complications, and in particular of death of a patient who has sustained an insult, such as surgery, burns, trauma, etc., or an infection generating a systemic inflammatory response syndrome (SIRS), in particular in a patient presenting a sepsis, especially a severe sepsis. Preferably, using a kit of the invention means that the risk of mortality in a patient who is in a state of septic shock can be evaluated.

The present invention also pertains to the use of the measurement, in vitro or ex vivo, of the quantity of at least one transcript of the IL7R gene, of at least one transcript of the IL7R gene corresponding to a mRNA, in a biological sample of a patient who has sustained an insult or an infection generating a systemic inflammatory response syndrome, to evaluate the risk of complications, and in particular of mortality, in said patient. In particular, said patient is in a septic state, especially severe or has undergone surgery, a burn or trauma generating a systemic inflammatory response syndrome. In accordance with particular implementations, the biological test sample is obtained from a patient in a state of septic shock or who has previously been in a state of septic shock within the 6 days preceding taking the biological test sample. Preferably, said at least one transcript of the IL7R gene is selected from the transcripts IL7R-001 of SEQ ID NO: 2, IL7R-002 of SEQ ID NO: 3, IL7R-003 of SEQ ID NO: 4, IL7R-005 of SEQ ID NO: 6, and IL7R-007 of SEQ ID NO: 8 and their variants, the sequence of a variant having at least 99% identity with one of said sequences. In particular, said at least one transcript of the IL7R gene is selected from transcripts comprising at least a portion of the transmembrane domain, or indeed the entire transmembrane domain, of CD127, and preferably corresponds to the transcript IL7R-001 of SEQ ID NO: 2 or to one of its variants having at least 99% identity with said sequence.

More broadly, all of the preferred implementations mentioned above concerning the method and combinations thereof also constitute preferred implementations as regards the use. The use of the invention could also include detecting and/or quantifying the transcript or transcripts of the selected IL7R gene, combined with estimating at least one SOFA and/or SAPSII severity score in order to evaluate the risk of complications in a patient who has sustained an insult or an infection generating a systemic inflammatory response syndrome (SIRS), and in particular in a patient who is in a state of septic shock. In this implementation, the SOFA score is preferably calculated as described by Vincent et al., 1996, and/or the SAPSII score is preferably calculated as described by Le Gall et al., 1993.

Any of the preferred implementations that are mentioned above concerning the method and combinations thereof also constitute preferred implementations, as pertaining to the kit of the invention and its use and the use of the measurement, in vitro or ex vivo, of the quantity of at least one transcript of the IL7R gene.

Figure 2:
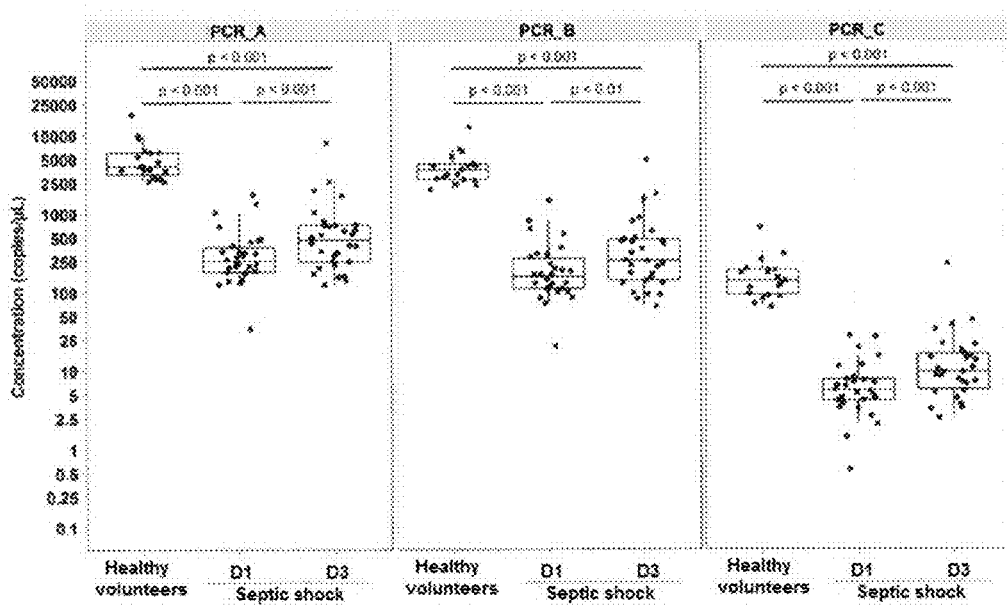

Various other characteristics become apparent from the following examples, made with reference to the accompanying figures that show, by way of non-limiting examples, embodiments of the subject matter of the invention:

FIG. 1 is a diagram showing the splicing of the messenger RNA of the IL7R gene;

FIG. 2 shows the levels of expression of various transcripts of the IL7R gene in healthy volunteers (n=19) and in patients in septic shock on D1 and D3 following the onset of septic shock (n=30). PCR-A: Transcripts IL7R-001, IL7R-002, IL7R-003, IL7R-005, IL7R-007; PCR-B: Transcript IL7R-001; PCR-C: Transcript IL7R-007. The Mann-Whitney test was used for the comparisons between healthy subjects and patients in septic shock on D1 or D3. The paired Wilcoxon test was used for the comparisons between D1 and D3 in the patients in septic shock.

Figure 3:
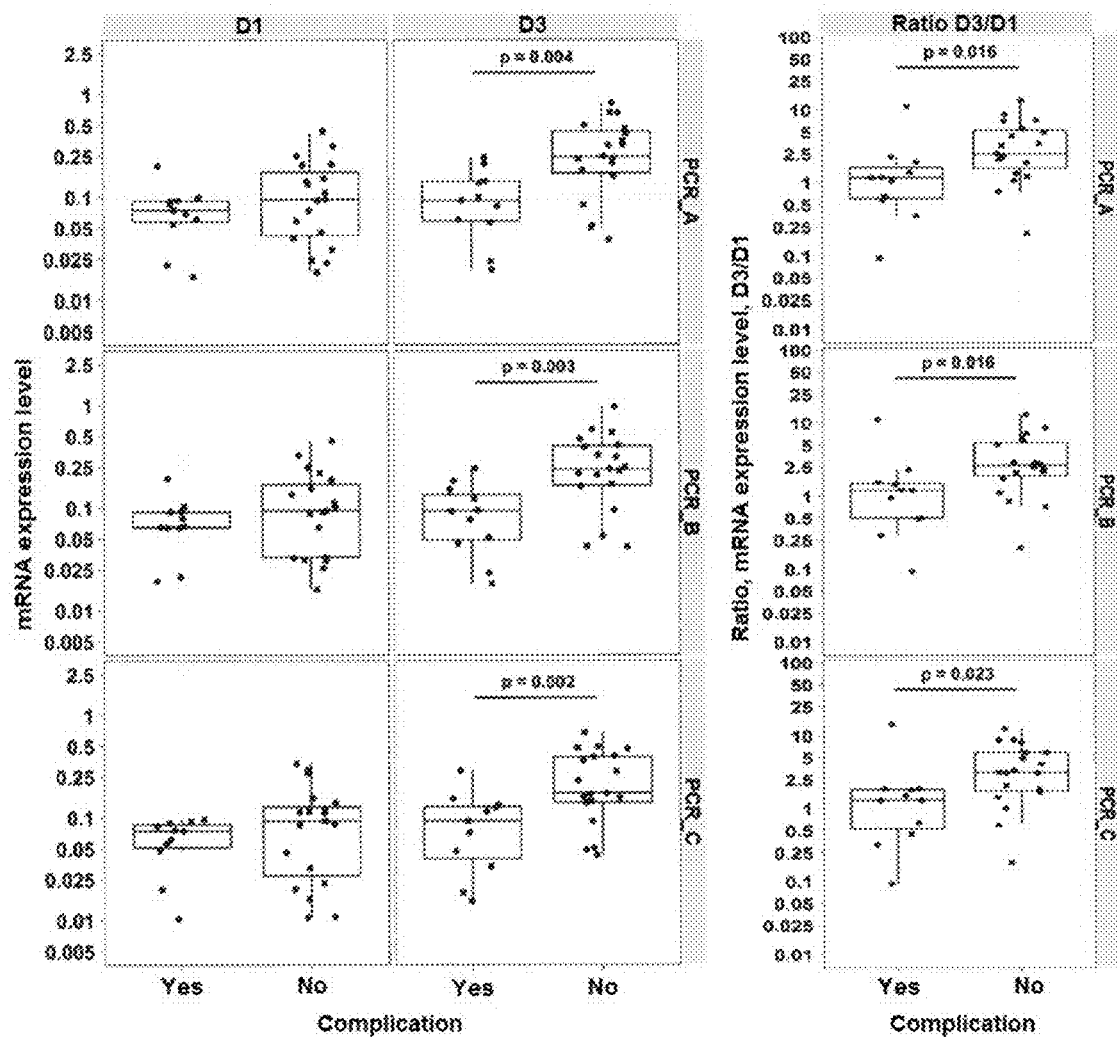

FIG. 3 shows the levels of expression for various transcripts of the IL7R gene as a function of the occurrence or not of complications in patients in septic shock, on D1, D3 or for the ratio D3/D1. The levels of expression are expressed as the "Calibrated Normalized Relative Quantity" (CNRQ) with HPRT1 as the reference gene, and were compared using the Mann-Whitney test. PCR-A: Transcripts IL7R-001, IL7R-002, IL7R-003, IL7R-005, IL7R-007; PCR-B: Transcript IL7R-001; PCR-C: Transcript IL7R-007.

Figure 4:
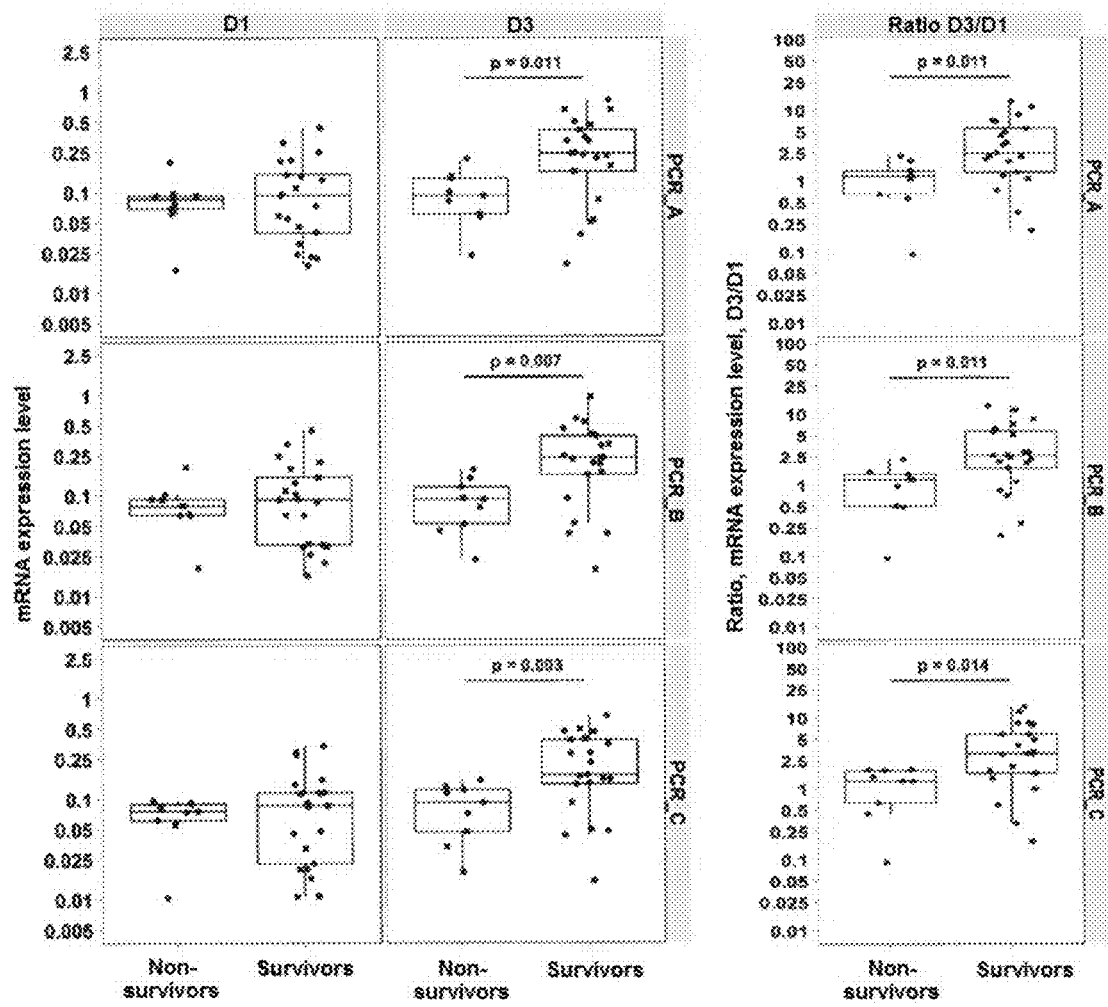

FIG. 4 shows the levels of expression for various transcripts of the IL7R gene as a function of the occurrence or not of death on D28 in patients in septic shock, on D1, D3 or for the ratio D3/D1. The levels of expression are expressed as CNRQ with HPRT1 as the reference gene, and were compared using the Mann-Whitney test. PCR-A: Transcripts IL7R-001, IL7R-002, IL7R-003, IL7R-005, IL7R-007; PCR-B: Transcript IL7R-001; PCR-C: Transcript IL7R-007.

METHODS

Patients and Biological Samples

Samples of whole blood were placed in PAXgene tubes (PreAnalytix) for 30 patients in septic shock on days 1 (D1) and 3 (D3) following the onset of septic shock, and then were stored (retrospective cohort).

On day 28 following admission to intensive care for septic shock, 9 patients had not survived ("NS") i.e. 30%, while 21 patients had survived ("S") out of the 30 patients.

During their stay in intensive care, 4 patients contracted a nosocomial infection, i.e. 13%, while 26 patients out of the 30 patients did not contract one.

In total, 11 patients suffered complications (death on D28 or suffered a nosocomial infection in intensive care) i.e. 37%, while for 19 patients out of the 30 patients, no complications occurred.

Samples of whole blood, processed in the same manner as for the samples from patients in septic shock, were also taken from 19 healthy volunteer subjects.

Detection Technique
Extraction of RNA and Reverse Transcription

RNA was extracted with the aid of a PAXgene Blood RNA (PreAnalytix) kit, following the manufacturer's recommendations. The quality of the extracted RNA was checked using a Bioanalyzer (Agilent Technologies, Santa Clara, CA), using RNA 6000 Nano chips. Before the RNA elution step, the residual genomic DNA was eliminated by the action of a DNAse. The quality of the RNA was then checked with the aid of a RNA 6000 Nano kit using a Bioanalyzer (Agilent Technologies); samples with a RIN (RNA Integrity Number) of more than 6 were considered to be good quality. Finally, the concentration of RNA was determined by fluorimetry (RNA assay kit from Qubit, Life Technologies).

The total RNA (200 nanograms (ng)) then underwent a reverse transcription into complementary DNA using the SuperScript® VILO™ cDNA Synthesis kit (Life Technologies, Chicago, IL). The cDNA solution obtained thereby was diluted by 1/20 and stored at −80° C. before the quantitative PCR reaction.

Quantitative PCR Technique

The PCR reactions were carried out on a LightCycler 480 (Roche Molecular Biochemicals, Basle, Switzerland) with the Taqman Fast Advanced Master Mix PCR kit (Roche), in a final volume of 20 microliters (µL) containing 0.5 moles (M) of primers and 0.1 M of probe. The PCR reactions were carried out with an initial denaturing step of 10 min at 95° C., followed by 45 amplification cycles of "touchdown PCR" (10 seconds (s) at 95° C., 29 s at 68° C. for the first cycle, with a reduction of 0.5° C. for each cycle until reaching 58° C., and extension for 1 s at 72° C.). The maximum second derivative method was used with the aid of LightCycler software in order to automatically determine the Cp ("crossing point") for each sample. Calibration curves were generated by producing a series of 8 1/10 dilutions of a standard stock solution of amplicon of known concentration. The primer pairs and probes used are listed in Table 2:

TABLE 2

Sequences of primers and probes for PCR for the detection of different transcripts of the IL7R gene

| | Sequences | Target transcripts |
| --- | --- | --- |
| PCR-A ("several transcripts") | Sense primer SEQ ID NO: 12<br>Anti-sense primer SEQ ID NO: 13<br>Probe SEQ ID NO: 14 | IL7R-001 (NM_002185)<br>IL7R-002 (ENST00000514217)<br>IL7R-003 (ENST00000506850)<br>IL7R-005 (ENST00000511031)<br>IL7R_007 (ENST00000511982) |
| PCR-B (membrane form) | Sense primer SEQ ID NO: 15<br>Anti-sense primer SEQ ID NO: 16<br>Probe SEQ ID NO: 17 | IL7R-001 (NM_002185) |
| PCR-C (potentially soluble form) | Sense primer SEQ ID NO: 18<br>Anti-sense primer SEQ ID NO: 19<br>Probe SEQ ID NO: 20 | IL7R-007 (ENST00000511982) |

The expression levels were expressed as the CNRQ ("Calibrated Normalized Relative Quantity"), as in Hellemans et al., 2007, including a reference gene and a calibrator. The reference gene used was HPRT1 (hypoxanthine phosphoribosyltransferase 1, NM_000194), measured by PCR (sense primer: CCAAAGATGGTCAAGGTCGC, anti-sense primer: GACACAAACATGATTCAAATCC, probe CAAGTTTGTTGTAGGATATGCCC). The calibrator was composed of a pool of RNA from healthy volunteers. This calibrator had undergone the same process as the clinical samples starting from the reverse transcription step.

Statistical Analyses

The statistical analyses were carried out with the aid of RStudio software (version 0.98.501). The differences observed were considered to be significant for p values of less than 0.05.

Descriptive Analysis of Expression Levels for Transcripts of the IL7R Gene

The comparisons of the expression levels for the transcripts of the IL7R gene were carried out using the Mann-Whitney test, except in the case of the comparisons between D1 and D3 in the patients in septic shock, which were carried out using the paired Wilcoxon test.

Analyses of the Capacity to Predict the Occurrence of Complications or Death on D28

The ROC (Receiver Operating Curves) graphs were generated and the areas under the curve as well as their confidence intervals were calculated.

Results

Detection of Transcripts of the IL7R Gene in Healthy Subjects and in Patients in Septic Shock The level of expression of the transcripts of the IL7R gene was measured as described above in samples of whole blood from 30 patients in septic shock and 19 healthy volunteer subjects. The results are shown in FIG. 2.

All of the transcripts of the IL7R gene were detected all at once in the healthy subjects and in the patients in septic shock, on D1 and D3 following the onset of septic shock.

The expression level for the transcript coding for the membrane form of CD127 (Transcript IL7R-001) was high compared with the transcript corresponding to a potentially soluble form (Transcript IL7R-007), in the healthy subjects as well as in the patients in septic shock.

The expression levels for the entirety of the transcripts measured using PCR-A were lower in the patients in septic shock on D1 and D3 compared with the healthy volunteers, and this was also the case for the transcript coding for the membrane form of CD127 (Transcript IL7R-001—PCR-B) and for the transcript corresponding to a potentially soluble form of CD127 (Transcript IL7R-007—PCR-C).

In the patients in septic shock, a significant increase was observed in the expression level for the various transcripts of the IL7R gene coding for CD127 between D1 and D3.

Comparison of Expression Levels of Transcripts of the IL7R Gene Coding for CD127 as a Function of the Occurrence of Complications in the Patients in Septic Shock As can be seen in FIG. 3, the expression levels for the various transcripts of the IL7R gene, including that coding for the membrane form (Transcript IL7R-001) and that corresponding to a potentially soluble form (Transcript IL7R-007), were significantly lower on D3 in the patients suffering from complications (death or confirmed nosocomial infection that corresponds to "yes" in FIG. 3). This observation is also true for the ratio of the expression levels, D3/D1.

Capacity of Transcripts of the IL7R Gene to Predict the Risk of Complications in Patients in Septic Shock The predictive capacity of the measurement of the expression levels of the various transcripts of the IL7R gene was studied in respect of the incident to be studied, namely the occurrence of complications. The results are shown in Table 3, which summarizes the areas under the ROC (Receiving Operating Curve) curve or AUC (Area Under Curve), as well as their 95% confidence intervals.

TABLE 3

Areas under the curve for the prediction of the risk of complications for the various transcripts of the IL7R gene

| Transcripts | Day | AUC | 95% CI |
|---|---|---|---|
| All transcripts | D1 | 0.632 | [0.425-0.840] |
| (PCR-A) | D3 | 0.813 | [0.657-0.970] |
|  | Ratio D3/D1 | 0.766 | [0.571-0.960] |
| Membrane transcript | D1 | 0.627 | [0.419-0.832] |
| IL7R-001 | D3 | 0.823 | [0.671-0.975] |
| (PCR-B) | Ratio D3/D1 | 0.766 | [0.570-0.961] |
| Soluble transcript | D1 | 0.665 | [0.464-0.866] |
| IL7R-007 | D3 | 0.837 | [0.689-0.986] |
| (PCR-C) | Ratio D3/D1 | 0.751 | [0.549-0.953] |

The expression levels for the various transcripts of the IL7R gene measured on D3, or the ratio of the expression, D3/D1, thus allowed patients who suffer from complications to be distinguished from those who do not suffer, with areas under the curve of more than 0.8 for D3 and more than 0.75 for the expression ratio D3/D1.

Comparison of Expression Levels for Transcripts of the IL7R Gene as a Function of the Occurrence of Death in Patients in Septic Shock As can be seen in FIG. 4, the expression levels for the various transcripts of the IL7R gene, including that coding for the membrane form (Transcript IL7R-001) and that corresponding to a potentially soluble form (Transcript IL7R-007), were significantly lower on D3 in patients who are going to die (denoted "Non-surviving" in FIG. 4) within 28 days following the septic shock, compared with the patients who survive (denoted "Survivors" in FIG. 4) more than 28 days. This observation is also true for the ratio of the expression levels, D3/D1.

Capacity of Transcripts to Predict the Risk of Death in Patients in Septic Shock The predictive capacity of the measurement of the expression levels for various transcripts of the IL7R gene was studied in respect of the occurrence of death within 28 days following the onset of septic shock. The results are shown in Table 4, which summarizes the areas under the ROC curve and their 95% confidence intervals.

TABLE 4

Areas under the curve for the prediction of the occurrence of death for the various transcripts of the IL7R gene

| Transcripts | Day | AUC | 95% IC |
|---|---|---|---|
| All transcripts | D1 | 0.545 | [0.327-0.763] |
| (PCR-A) | D3 | 0.794 | [0.629-0.958] |
|  | Ratio D3/D1 | 0.794 | [0.633-0.954] |
| Membrane transcript | D1 | 0.550 | [0.335-0.765] |
| IL7R-001 | D3 | 0.809 | [0.653-0.966] |
| (PCR-B) | Ratio D3/D1 | 0.794 | [0.631-0.956] |
| Soluble transcript | D1 | 0.603 | [0.394-0.812] |
| IL7R-007 | D3 | 0.836 | [0.692-0.980] |
| (PCR-C) | Ratio D3/D1 | 0.783 | [0.619-0.947] |

The expression levels for various transcripts of the IL7R gene measured on D3, or the ratio of the expression, D3/D1, can thus be used to discriminate patients who are going to die from those who are going to survive, with areas under the curve of more than 0.75.

This study shows that the expression levels for various transcripts of the IL7R gene can be used to identify patients the most at risk of suffering from complications after a septic shock. More precisely, on D3, the patients in whom complications are going to occur have lower expression levels for transcripts of the IL7R gene than patients who do not suffer from any complications. The change in the expression levels for the various transcripts of the IL7R gene between D1 and D3 is also informative; the expression levels remain stable in patients who are going to suffer from complications, while they increase in patients who are not going to suffer from any complications. Although on a protein level, only the soluble form was associated with a poor prognosis (Venet et al., 2012), the various transcripts of the IL7R gene, which correspond to the membrane form or to soluble forms, and that are assayed simultaneously or individually, are capable of identifying patients who are at the greatest risk of the occurrence of complications.

REFERENCES

Bio-Rad Laboratories, 2006, Real-Time PCR: Applications Guide.
Bone, R. C., et al., 1992, Chest 101, 1644-1655.
Boom, R., et al., 1990, J. Clin. Microbiol. 28, 495-503.
Buh Gasparic, M., et al., 2010, Anal. Bioanal. Chem. 396, 2023-2029.
Carini, C., et al., 1994, Eur. J. Immunol. 24, 2927-2934.
Chee, M., et al., 1996, Science 274, 610-614.
Cheng, J., et al., 1998, Nat. Biotechnol. 16, 541-546.
Cheng, J., et al. 1996, Mol. Diagn. J. Devoted Underst. Hum. Dis. Clin. Appl. Mol. Biol. 1, 183-200.
Clontech, 2003, BD QZyme Assays for Quantitative PCR.
Cloonan, N., et al., 2008, Nat. Methods 5, 613-619.
Duck, P., et al., 1990, BioTechniques 9, 142-148.
Emrich, S. J., et al., 2007, Genome Res. 17, 69-73.
Espy, M. J., et al., 2006, Clin. Microbiol. Rev. 19, 165-256.
Ginot, F., 1997, Hum. Mutat. 10, 1-10.
Goblet, C., et al., 1989, Nucleic Acids Res. 17, 2144.
Goodwin, R. G., et al., 1990, Cell 60, 941-951.
Heid, C. A., et al., 1996, Genome Res. 6, 986-994.
Hellemans, J., et al., 2007, Genome Biol. 8, R19.
Holland, P. M., et al., 1991, Proc. Natl. Acad. Sci. U.S.A. 88, 7276-7280.
Jiang, Q., et al., 2005, Cytokine Growth Factor Rev. 16, 513-533.
Keller G. H., et al., 1993), Stockton Press.
Kricka, L. J., 1999, Clin. Chem. 45, 453-458.
Le Gall, J. R., et al., 1993, J. Am. Med. Assoc. 270, 2957-2963.
Levison, P. R., et al., 1998, J. Chromatogr. A 827, 337-344.
Livache, T., et al., 1994, Nucleic Acids Res. 22, 2915-2921.
Mhlanga, M. M., and Malmberg, L., 2001, Methods San Diego Calif. 25, 463-471.
Mortazavi, A., et al., 2008, Nat. Methods 5, 621-628.
Nazarenko, I., et al., 2002, Nucleic Acids Res. 30, e37.
Nazarenko, I. A., et al., 1997, Nucleic Acids Res. 25, 2516-2521.
Park, L. S., et al., 1990, J. Exp. Med. 171, 1073-1089.
Pease, A. C., et al., 1994, Proc. Natl. Acad. Sci. U.S.A. 91, 5022-5026.
Ramsay, G., 1998), Nat. Biotechnol. 16, 40-44.
Rose, T., et al., 2009, J. Immunol. 182, 7389-7397.
Sigma, 2008, qPCR Technical Guide.
Venet, F., et al., 2012, J. Immunol. 189, 5073-5081.
Vincent, J. L., et al., 1996, Intensive Care Med. 22, 707-710.
Vranjkovic, A., et al., 2007, Int. Immunol. 19, 1329-1339.

The invention claimed is:

1. A kit for the in vitro measurement of a quantity of at least one transcript of the IL7R gene in a biological blood sample, comprising:
specific reagents for measuring the quantity of said at least one transcript of the IL7R gene in said biological blood sample, said at least one transcript comprising the transcript IL7R-001 of SEQ ID NO: 2, or a variant of the transcript IL7R-001 of SEQ ID NO: 2 having at least 99% identity with said sequence, including the following amplification primer pair: forward primer with SEQ ID NO: 12 and reverse primer with SEQ ID NO: 13 and a probe with SEQ ID NO: 14, said probe being either tagged with a marker, or immobilized on a solid support; and
a blood control sample that is a blood sample that is calibrated and contains the quantity of said at least one transcript of the IL7R gene that corresponds to the mean quantity measured in a pool of reference blood samples from human patients who are in a state of septic shock when the reference blood samples are taken, or who were in a state of septic shock within 72 hours after the reference blood samples were taken, and who were known to have survived, and/or a blood control sample that is a blood sample that is calibrated and contains the quantity of said at least one transcript of the IL7R gene that corresponds to the mean quantity measured in a pool of reference blood samples from human patients who are in a state of septic shock when the reference blood samples are taken, or who were in a state of septic shock within 72 hours after the reference blood samples were taken, and who were known not to have survived.

2. The kit according to claim 1, comprising another blood control sample that is calibrated and contains the quantity of said at least one transcript of the IL7R gene that corresponds to the mean quantity measured in a pool of reference blood samples from human patients who were in a state of septic shock within 24 hours after the reference blood samples were taken, and who were known to have survived, and/or a blood control sample that is a blood sample that is calibrated and contains the quantity of said at least one transcript of the IL7R gene that corresponds to the mean quantity measured in a pool of reference blood samples from human patients who were in a state of septic shock within 24 hours after the reference blood samples were taken, who were known not to have survived.

3. The kit according to claim 1, further comprising the following amplification primer pair: a forward primer with SEQ ID NO: 15 and a reverse primer with SEQ ID NO: 16.

4. The kit according to claim 3, further comprising a probe with SEQ ID NO: 17.

5. The kit according to claim 1, further comprising the following amplification primer pair: a forward primer with SEQ ID NO: 18 and a reverse primer with SEQ ID NO: 19.

6. The kit according to claim 5, further comprising a probe with SEQ ID NO: 20.

* * * * *